(12) United States Patent
Poras et al.

(10) Patent No.: US 11,648,231 B2
(45) Date of Patent: May 16, 2023

(54) AMINO ACID DERIVATIVES CONTAINING A DISULFANYL GROUP IN THE FORM OF AN NEP AND APN INHIBITOR FOR THE PREVENTION AND TREATMENT OF TRIGEMINAL NERVE PAIN

(71) Applicant: PHARMALEADS, Paris (FR)

(72) Inventors: Hervé Poras, Villepreux (FR); Tanja Ouimet, Paris (FR); Marie Claude Fournie Zaluski, Paris (FR); Bernard Roques, Paris (FR); Michel Wurm, Royat (FR)

(73) Assignee: PHARMALEADS, Paris (FR)

(*) Notice: Subject to any disclaimer, the term of this patent is extended or adjusted under 35 U.S.C. 154(b) by 33 days.

(21) Appl. No.: 16/964,779

(22) PCT Filed: Jan. 25, 2019

(86) PCT No.: PCT/EP2019/051904
§ 371 (c)(1),
(2) Date: Jul. 24, 2020

(87) PCT Pub. No.: WO2019/145507
PCT Pub. Date: Aug. 1, 2019

(65) Prior Publication Data
US 2021/0052539 A1 Feb. 25, 2021

(30) Foreign Application Priority Data

Jan. 26, 2018 (FR) ...................................... 1850630

(51) Int. Cl.
| | | |
|---|---|---|
| *A61K 31/265* | (2006.01) | |
| *A61P 25/06* | (2006.01) | |
| *A61K 31/135* | (2006.01) | |
| *A61K 31/138* | (2006.01) | |
| *A61K 31/195* | (2006.01) | |
| *A61K 31/197* | (2006.01) | |
| *A61K 31/352* | (2006.01) | |
| *A61K 31/36* | (2006.01) | |
| *A61K 31/485* | (2006.01) | |
| *A61K 31/53* | (2006.01) | |
| *A61K 31/55* | (2006.01) | |
| *A61K 31/5513* | (2006.01) | |
| *A61K 45/06* | (2006.01) | |

(52) U.S. Cl.
CPC .......... *A61K 31/265* (2013.01); *A61K 31/135* (2013.01); *A61K 31/138* (2013.01); *A61K 31/195* (2013.01); *A61K 31/197* (2013.01); *A61K 31/352* (2013.01); *A61K 31/36* (2013.01); *A61K 31/485* (2013.01); *A61K 31/53* (2013.01); *A61K 31/55* (2013.01); *A61K 31/5513* (2013.01); *A61K 45/06* (2013.01); *A61P 25/06* (2018.01)

(58) Field of Classification Search
CPC .... A61K 31/265; A61K 31/35; A61K 31/138; A61P 25/06
See application file for complete search history.

(56) References Cited

U.S. PATENT DOCUMENTS

| | | | |
|---|---|---|---|
| 6,518,260 B1 | 2/2003 | Fournie-Zaluski et al. | |
| 8,247,609 B2 * | 8/2012 | Roques .................. | A61P 25/24 564/463 |
| 8,466,309 B2 * | 6/2013 | Fournie-Zaluski ... | C07C 323/60 560/147 |
| 9,388,129 B2 | 7/2016 | Roques et al. | |
| 2009/0012153 A1 | 1/2009 | Roques et al. | |
| 2009/0131509 A1 | 5/2009 | Roques et al. | |
| 2011/0071218 A1 | 3/2011 | Fournie-Zaluski et al. | |
| 2011/0124601 A1 | 5/2011 | Roques et al. | |
| 2015/0299116 A1 | 10/2015 | Roques et al. | |
| 2018/0305308 A1 | 10/2018 | Poras et al. | |

FOREIGN PATENT DOCUMENTS

| | | |
|---|---|---|
| FR | 2997081 A1 | 4/2014 |
| WO | WO-98/18803 A1 | 5/1998 |
| WO | WO-2007/048787 A1 | 5/2007 |
| WO | WO-2009/138436 A1 | 11/2009 |
| WO | WO-2010/010106 A1 | 1/2010 |
| WO | WO-2014/064166 A1 | 5/2014 |
| WO | WO-2017/064250 A1 | 4/2017 |

OTHER PUBLICATIONS

"Pharmaleads to Present PL265 for Ocular Pain Resultsat the ARVO 2017 Annual Meeting in Baltimore", May 5, 2017 (May 5, 2017), Retrieved from teh Internet at:<URL:http://www.pharmaleads.com/wp-content/uploads/2017/05/Pharmaleads-ARVO-2017-5.05.17-FINAL.pdf (2017).

Thibault K et al, "Antinociceptive and anti-allodynic effects of oral PL37, a complete inhibitor of enkephalin-catabolizing enzymes, in a rat model of peripheral neuropathic pain induced by vincristine", Dec. 14, 2018, vol. 600. No. 1-3, p. 71-77.

HervéPoras et al, "New Orally Active Dual Enkephalinase Inhibitors (DENKIs) for Central and Peripheral Pain Treatment", *Journal of Medicinal Chemistry*,vol. 57, No. 13, Jun. 24, 2014, p. 5748-5763.

Meunier A et al, "Attenuation of pain-related behavior in a rat model of trigeminal neuropathic pain by viral-driven enkephalin overproduction in trigeminal ganglion neurons", Molecular Therapy : The Journal of the American Society of Gene Therapy, Academic Press ; Nature Publishing Group, US, vol. 11, No. 4, Apr. 1, 2005, p. 608-616.

(Continued)

*Primary Examiner* — Kevin E Weddington
(74) *Attorney, Agent, or Firm* — Marshall, Gerstein & Borun LLP

(57) ABSTRACT

The present invention concerns a pharmaceutically acceptable salt of a compound of the following formula (I): $H_2N-CH(R_1)-CH_2S-S-CH_2-CH(R_2-CONH-CH(R_3)-COOR_4$ (I) and more particularly an acid addition salt thereof, and the compositions comprising the same, for use in the prevention or treatment of trigeminal nerve pain, in particular migraines or trigeminal neuralgia.

14 Claims, 3 Drawing Sheets

(56) References Cited

OTHER PUBLICATIONS

Poras Hervéet al, "Modulation of disulfide dual ENKephalinase inhibitors (DENKIs) activity by a transient N-protection for pain alleviation by oral route", European Journal of Medicinal Chemistry, Editions Scientifique Elsevier, Paris, FR, vol. 102, Jul. 17, 2015, p. 58-67.
International Search Report, corresponding International Application No. PCT/EP2019/051904, dated Apr. 25, 2019.
Written Opinion of the International Research Administration, corresponding to International Application No. PCT/EP2019/051904, dated Apr. 25, 2019.
Lipton et al., Trends, "Estimated Prevalence and Distribution of Reported Orofacial Pain in the Unites States" *J Am Dental Assoc* (1993), 124: 115-121.
Macfarlane et al., "Orofacial Pain: just another Chronic Pain?" Pain, (2002), 99: 453-458.
Torsten et al., "Widespread pain as a risk factor for dysfunctional temporomandibular disorder pain" *Pain* (2003), 102: 257-263.
Dworkin et al., Epidemiology of signs and symptoms in temporomandibular disorders: clinical signs in cases and controls: *J Am Dent Assoc* (1990), 120: 273-281.
Pau et al., Prevalence Estimates and Associated Factors for Dental Pain: A Review *Oral Health & Preventive Dentistry* (2003), vol. 1: No. 3, 209-220.
Bereiter et al., "Trigeminal Mechanisms of Nociception: Peripheral and Brainstem Organization" *The senses, a comprehensive reference* (2008), vol. 5: pp. 435-460 Academic Press San Diego, CA.
Goadsby et al., "Pathophysiology of Migrane: A Disorder of Sensory Processing" *Physiol. Rev.* (2017), 97: 553-622, Feb. 8, 2017.
Hu XH et al.,"Burden of Migrane in the United States" *Arch Intern Med* (1999), vol. 159 (8): 813-818, Apr. 26, 1999.
Scher IA et al., "Factors associated with the onset and remission of chronic daily headache in a population-based study" *Pain* (2003), 106: pp. 81-89.
Ashkenasi A et al., "Identifying cutaneous allodynia in chronic migrane using a practical clinical method" NIH, *Cephalalgia February* (2007), vol. 27; 111-117.
Schwedt TJ et al., "Episodic and Chronic Migraineurs are Hypersensitive to thermal stimuli between migraine attacks" *NIH, Cephalalgia January* (2011), 31: 6-12.
Bigal Me et al., "What predicts the change from episodic to chronic migraine?" *Curr Opin Neurol* (2009), 22: pp. 269-276.
Loder E et al.,"The 2021 AHS/AAN Guidelines for Prevention of Episodic Migraine" Headache (2012), 52: pp. 930-945.
Stovner etal., "A comparative study of candesartan versus propranolol for migraine prophylaxis"Cephalalgia (2014),vol. 34: 523-532.
Lipton RB et al., "Migraine prevalence, Disease burden, and the need for preventive therapy" Neurology (2007), 68(5) 343-349.
Silberstein SD, "Preventive Migraine Treatment" Review Article Continuum (2015), 21(4): 973-989.
Montano et al., "Advances in diagnosis and treatment of trigeminal neuralgia" Therapeutics and Clinic Risk Manag (2015), 11: 289-299.
Truini et al., "a mechanism-based classification of pain in multiple sclerosis" Review, Springer, J Neurol (2013), 260: 351-367.
Duffy et al., Review Article, The Contribution of Immune and Glial Cell Types in Experimental Autoimmune Encephalomyelitis and Multiple Sclerosis Multiple Sclerosis Int (2014) 285245, 17 Pages.
Thorburn et al., "Facial hypersensitivity and trigeminal pathology in mice with experimental autoimmune encephalomyelitis" Pain (2016), 157(3): 627-642.
Hugues et al., "Identification of two related pentapeptides from the brain with potent opiate agonist activity" Nature (1975), 258, 577?579.
Waterfield et al., "Opioid activities of fragments" Eur J Pharmacol (1979), 58: 11-18.
Waksman et al., "Autoradiographic comparison of the distribution of the neutral endopeptidase enkephalinase" Proc Natl Acad Sci USA (1986), 83: 1523-1527.
Belluzi et al., "Analgesia induced in vivo by central administration of encephalin in rat" Nature (1976), 260: 625-626.
Malfroy et al., "High-affinity encephalin-degrading peptidase in brain is increased after morphine" Nature (1978), 276: 523-526.
Waksman et al., "In vitro and in vivo effects of kelatorphan on encephalin metabolism in rodent brain" European Journal of Pharmacology (1985), 117: 233-243.
Bourgoin et al., "Effects of Kelatorphan and Other Peptidase Inhibitors on In vitro and in vivo release" Journal of Pharmacology Experimental Therapeutics (1986), 238 (1), 360-366.
Roques, "Novel approaches to targeting neuropeptide system"Trends Pharmacology Sci (2000), 21, 475-483.
Emily M. Jutkiewicz, "RB101-medicated Protection of Endogenous Opioids: Potential Therapeutic Utility?" CNS Drug Reviews (2007), 13, 192-205.
Wang et al., "Endomorphin-1 and Endomorphin-2 Modulate Responses of Trigeminal Neurons" Journal Neurophysiology (2000), 83 : 3570-3574.
Charles & Pradhan, "Delta-opioid receptors as targets for migraine therapy" Current Opinion (2016), 29: 314-319.
Pradhan et al., "?-Opioid receptor agonists inhibit migraine-related hyperalgesia, aversive state and cortical spreading depression in mice" Research Paper, British Journal Pharmacology (2014), 171: 2375-2384.
Da Silva et al., "Migraine and the Mu-Opioidergain System" Curr Pain Headache Rep (2014), 18: pp. 1-10.
Mosnaim et al., "Plasma Methionine Enkephalin" Headache (1986), 26: 278-281.
Storer et al., "Characterization of opioid receptors that modulate nociceptive neurotransmission in the trigeminocervical complex" British J Pharmacol (2003), 138: 317-324.
Menon et al., The human μ-opioid receptor gene polymorphism (A118G),J Headache Pain (2012), 13:513-519.
Baillie et al., "Peripheral μ-opioid receptor medicated inhibition of calcium signaling" Neuropharmacol (2015), 93: 267-273.
Siberstein, "Opioids" Review, Cephalalgia (2000), 20: 854-864.
Williamson et al., "Role of opioid receptors in neurogenic dural vasodilation and sensitization of trigeminal neurons in anaesthetized rats" British J Pharmacology (2001), 133: 807-814.
Hao et al., "Transgene-mediated encephalin release enhances the effect of morphine and evades tolerance to produce a sustained antiallodynic effect in neuropathic pain" Pain (2003), 102: 135-142.
Bonnard et al., "Long-lasting oral analgesic effects of N-protected aminophosphinic duel ENKephlinase inhibitors (DENKIs) in peripherally controlled pain" Pharmacology Research Perpective (2015), 3(2), e00116, pp. 1-7.
Headache Classification Committee of the International Headache Society (IHS). The International Classification of Headache Disorders, 3rd edition, Cephalalgia (2013), 33: 629-808.
Tso AR et al.,"Anti-CGRP Monoclonal Antibodies: the Next Era of Migraine Prevention?" Curr Treat Options Neurol (2017), 19: Jun. 27, pp. 1-11.
Zakrzewska JM et al., "Safety and efficacy of a Nav1.7 selective sodium channel blocker in patients with trigeminal neuralgia" Lancet Neurology (2017), 16: 291-300.
Piomelli et al. "the endocannabinoid system as a target for therapeutic drugs" Review, TIPS (2000), 21: 218-224.
Aicher et al., "Hyperalgesia in an animal model of multiple sclerosis" Pain (2004), 110: 560-570.
PLP, R&D Systems, Proteolipid Protein Myelin, fragment 139-151.
Guy et al., "Are there differences between cephalic and extracephalic cutaneous allodynia in migraine patients?" Cephalalgia (2010), 30: 881-886.
Lovatti et al., "Allodynia in migraine: frequent random association or unavoidable consequence?" Expert Review Neurother (2009), 9: 395-408.
Louter et al., "Cutaneous allodynia as predictor of migraine chronification" Brain, A Journal of Neurology (2013), 136: 3489-3496.

(56) References Cited

OTHER PUBLICATIONS

Boyer et al., "General trigeminospinal central sensitization and impaired descending pain inhibitory controls contribute to migraine progression" Pain (2014), 155: 1196-1205.

Dallel et al., "Recurrent administration of the nitric oxide donor" Cephalalgia (2017), pp. 1-10, Jan 1.

Hansen & Olesen, "Towards a pragmatic human migraine model for drug testing" Cephalalgia (2017), 37: 11-19.

* cited by examiner

AMINO ACID DERIVATIVES CONTAINING A DISULFANYL GROUP IN THE FORM OF AN NEP AND APN INHIBITOR FOR THE PREVENTION AND TREATMENT OF TRIGEMINAL NERVE PAIN

CROSS-REFERENCE TO RELATED APPLICATIONS

This application is a U.S. National stage of International Patent Application No. PCT/EP2019/051904 filed Jan. 25, 2019, which claims the benefit of priority of French Patent Application No. 1850630 filed Jan. 26, 2018, the respective disclosures of which are each incorporated herein by reference in their entireties.

BACKGROUND

Field of the Disclosure

The present invention relates to mixed disulfide compounds comprising an NEP inhibitor and an APN inhibitor (on either side of a disulfide bridge) for their use for the prevention and/or treatment of trigeminal nerve pains.

Technological Background

The Trigeminal Nerve

Pain is a nociceptive response related to local stimulation in the body. The perception thereof in the central nervous system requires the transmission of pain stimuli by the peripheral nerve fibers. When the tissues are stimulated, whether by thermal, mechanical or chemical stimuli, electrochemical signals are transmitted from the sensory nerve endings to the spinal column and then to the brain where the pain is felt.

There are different types of pain, of widely varied origin whose treatments are radically different depending on the type of pain and its etiology.

The trigeminal system, for example, is involved in nociceptive phenomena originating from oral, facial and cranial areas, but with very specific nociception characteristics, which has an impact on treatment. Indeed, craniofacial structures such as the cornea, the meninges and the dental pulp give rise to painful sensations in humans, but the most frequently encountered, such as dental pain, are often difficult to localize, and some headaches may occur even in the absence of any identifiable external cause.

The trigeminal nerve, the fifth pair of cranial nerves, is made up of three branches: the ophthalmic (V1), maxillary (V2), and mandibular (V3) divisions. Each division innervates one of the three dermatomes of the face as well as the underlying mucosal, vascular, muscle and meninges tissues. In all mammals, the ophthalmic branch, solely sensory, innervates the cornea, the neighboring conjunctiva, the tip of the nose, the intranasal mucosa, the upper eyelid and the supraorbital skin, a part of the meninges (dura mater and blood vessels) as well as the skin of the forehead and the scalp. The maxillary division, also solely sensory, innervates the infraorbital and postorbital skin, the upper lip, the alae of the nose, the intraoral maxillary mucosa and the teeth of the upper jaw. The mandibular branch, both sensory and motor, innervates the temporomandibular joint, the skin of the lower lip, the intraoral mandibular mucosa, the teeth of the lower jaw and the anterior part of the tongue. The transmission of acute pain involves the activation of various sensory receptor groups on peripheral A$\delta$ and C fibers as well as nociceptors, which respond to adverse mechanical, thermal and chemical stimuli.

The sensory pathways that transmit craniofacial nociceptive stimuli to higher stages of the brain originate from trigeminal ganglion nociceptors and their associated nuclei in the sensory complex of the trigeminal brainstem and upper cervical spinal cord. These structures simultaneously collect basic activities coming from numerous sources that are not only relevant for pain, but which may also play a role in the continuous transmission of crucial information to maintain the integrity of the craniofacial regions. Certain specific characteristics of trigeminal nociception may therefore result not only from the unique anatomical and functional organization of the nuclei of the trigeminal brainstem, but also from the interaction between central ascending and descending mechanisms.

Orofacial pain disorders constitute a major and costly component of healthcare and have a high prevalence with a disproportionally devastating impact on quality of life (American Department of Health and Human Services, 2000) "... oral health means much more than healthy teeth. It means being free of chronic oral-facial pain conditions . . . ". Community surveys indicate that many subjects generally report pain in the orofacial region, with estimates of more than 39 million, or 22% of the adult population, in the United States alone (Lipton et al., *J Am Dental Assoc* (1993), 124: 115-121). Other population surveys conducted in the United Kingdom (Macfarlane et al., *Pain* (2002), 99: 453-458), Germany (Torsten et al., *Pain* (2003), 102: 257-263) or regional pain centers in the United States (Dworkin et al., *J Am Dent Assoc* (1990), 120: 273-281) report similar levels (Pau et al., *Oral Health & Preventive Dentistry* (2003), 1: 209-220). Moreover, orofacial pain originates from numerous specific target tissues, such as the meninges, the cornea, the dental pulp, the oral and nasal mucosa, and the temporomandibular joint and therefore have several specific physiological characteristics relative to the nociceptive system connected to the spinal cord (Bereiter et al., *The senses, a comprehensive reference* (2008), vol. 5: 435-460 Academic Press San Diego, Calif.).

Trigeminal neuralgia (TN) is a common cause of acute recurrent headache, particularly involving women age 50 or older. It leads to significant pain, which can be very debilitating and a major source of psychological distress in severe cases. Its incidence is around twenty annual cases per 100,000 inhabitants. It is twice as common in women and its frequency increases with age.

There are two types of trigeminal neuralgia. Essential neuralgia, where the pain is unilateral, involves a part of the face corresponding to one of the sensory territories of the trigeminal. It is blazing, very intense, like burning or electrical shock, typically lasting a few seconds to a few minutes. Symptomatic trigeminal neuralgia is not generally paroxysmal but rather background pain. It also involves several regions of the trigeminal nerve.

Another pain associated with the trigeminal nerve, migraines represent one of the most common human disorders, involving 10 to 15% of the adult population with a clear predominance in women. Migraine is a neurological disorder associated with episodal manifestations or attacks, typically characterized by severe headaches lasting 4 to 72 hours, accompanied by malfunction of the autonomous nervous system and various neurological problems such as cutaneous allodynia (Goadsby et al., *Physiol. Rev.* (2017), 97: 553-622). When these problems are occasional, random, irregularly spaced and their number does not increase over time, they are called acute migraines. In some cases, the frequency of attacks increases, becoming chronic, a very debilitating form defined by headaches for 15 days or more a month. These are called chronic migraines.

Migraine attacks often lead to difficulty, even inability to live normally. Migraine sufferers often isolate themselves in a quiet and dark area. The financial burden is also enormous for society. The annual use of healthcare may exceed a billion dollars for migraine patients, while the lost productivity for employers may reach billions of dollars (Hu X H et al., *Arch Intern Med* (1999), 159 (8): 813-818). Certain comorbidities are present in migraine patients with a higher prevalence, such as stroke, angina pectoris, epilepsy, and some psychiatric disorders such as depression and anxiety.

Clinical studies have identified risk factors for chronic migraine. One is the frequency of headache attacks (Scher I A et al., *Pain* (2003), 106: 81-89), another is cutaneous allodynia. Two-thirds of migraines present allodynia, during (Ashkenasi A et al., *Cephalalgia* (2007), 27; 111-117) and between migraine attacks (Schwedt T J et al., *Cephalalgia* (2011), 31: 6-12). The development and severity of cutaneous allodynia are associated with frequent migraine attacks and are predictive of chronic migraine (Bigal M E et al., *Curr Opin Neurol* (2009), 22: 269-276).

Migraine treatment therefore should be initiated at the start of the attack, as early as possible. Grade 1 analgesics and NSAIDs (nonsteroidal antiinflammatory drugs) are sufficient for moderate forms. For patients whose attacks are more intense, treatment requires the use of triptans, such as sumatriptan, oral or injectable, to directly treat headache.

In cases of chronic migraines, prophylactic agents leading to a reduction in the frequency and severity of attacks are often prescribed. Propranolol, a beta blocker, has been one of the most commonly used preventative medications for a long time (Loder E et al., *Headache* (2012), 52: 930-945); this treatment reduces headache frequency in nearly 50% of patients (Stovner L J et al., *Cephalalgia* (2014), 34: 523-532). However, its mechanism and site of action remain poorly understood.

Although millions of Americans suffer migraines, only around 3% to 13% of them are on a preventative treatment, even though 38% could use a preventative agent (Lipton R B et al., *Neurology* (2007), 68(5) 343-349). Pharmacological interventions in the treatment of migraines comprise an acute treatment, for purposes of ending attacks, and a daily preventative treatment. The 2000 US Headache Consortium defined the following objectives regarding preventative treatment: (1) decrease attack frequency by 50% and decrease intensity and duration; (2) improve responsiveness to acute therapy; (3) improve function and decrease disability; and (4) prevent the occurrence of analgesic medication overuse headaches and prevent the occurrence of chronic headaches. Beta blockers such as propranolol are the most commonly used class of migraine prophylactic medications and are effective in 50% of cases, but others, such as tricyclic antidepressants, calcium channel blockers, CGRP antagonists, antiepileptics and nonsteroidal antiinflammatory drugs can also be used. (Silberstein S D, *Continuum* (2015), 21(4): 973-989).

Disorders such as multiple sclerosis may cause secondary trigeminal neuralgia.

The treatment of essential trigeminal neuralgia is mainly medical and sometimes surgical. Medical treatment uses carbamazepine as a first-line treatment, with progressive dose increase up to the minimum effective dose. Other drugs are used: oxcarbazepine, baclofen, clonazepam, lamotrigine, gabapentin or pregabalin.

Various medications and surgical procedures have been used for treatment of trigeminal neuralgia (TN). Despite the numerous available approaches, the results are far from satisfactory. Moreover, a certain number of patients become drug resistant, which requires surgical treatment to treat the neuralgia. However, pain frequently recurs after one or more surgical procedures (Montano et al., *Ther Clin Risk Manag* (2015), 11: 289-299).

Pain related to multiple sclerosis may be nociceptive or neuropathic, or a mixture thereof. Specific conditions include trigeminal neuralgia and Lhermitte's sign. These are associated with extreme pain, painful tonic spasms, optical nerve pain, muscle pain and migraines (Truini et al., *J Neurol* (2013), 260: 351-367).

Experimental autoimmune encephalitis (EAE) is the most widely used experimental model of multiple sclerosis. It shares numerous pathological characteristics with human cases, such as neuroinflammation and demyelinization and neuron damage (Duffy et al., *Mult Scler Int* (2014) 285245. doi: 10.1155/2014/285245). Although it is not completely clear, it seems that the pain generated in this model is the result of inflammation, glial activation and demyelinization (Olechowski et al., *Pain* (2009), 141: 156-164) as well as a process related to the trigeminal nerve (Thorburn et al., *Pain* (2016), 157(3): 627-642).

The Analgesic Effect of Enkephalins

Perception, transmission and regulation of nociceptive impulses depend on several neurotransmitters, especially enkephalins (met-enkephalin and leu-enkephalin). These are endogenous opioid pentapeptides, initially found in mammal brains (Hugues et al., *Nature* (1975), 258, 577-579). They are mainly related to two receptor classes, µ and δ opioid receptors (Waterfield et al., *Eur J Pharmacol* (1979), 58: 11-18) with different functions and locations (Waksman et al., *Proc Natl Acad Sci USA* (1986), 83: 1523-1527).

The antinociceptive properties of enkephalins have been demonstrated after intracerebroventricular administration of exogenous enkephalins (Belluzi et al., *Nature* (1976), 260: 625-626). However, this response is very fleeting due to rapid enzyme metabolization of these peptides. Synthetic enkephalin analogs, modified to make them resistant to enzymatic degradation, have shown antinociceptive properties equal to those of morphine, but have also presented the same adverse side effects.

Moreover, it is known that enkephalins (tyr-gly-gly-phe-met and tyr-gly-gly-phe-leu) are physiologically deactivated by two zinc metallopeptidases, neprilysin (EC 3.4.24.11, NEP) which cleaves the $gly^3$-$phe^4$ bond (Malfroy et al., *Nature* (1978), 276: 523-526) and aminopeptidase N (EC 3.4.11.2, APN) which cleaves the $tyr^1$-$gly^2$ bond of these peptides (Waksman et al., *Eur J Pharmacol* (1985), 117: 233-243).

The inhibition of these two enzymatic activities, by completely protecting enkephalins (Bourgoin et al., *J Pharm Exp Ther* (1986), 238 (1), 360-366), display the analgesic and antidepressant pharmacological activities of endogenous opiates, the enkephalins (Rogues, *Trends Pharmacol Sci* (2000), 21, 475-483; Jutkiewicz, *CNS Drug Rev* (2007), 13, 192-205).

Interactions Between the Enkephalinergic System and the Trigeminal Nerve

Opioid receptors are present in the caudate nucleus of the rat and cat trigeminal (Wang, *J Neurophysiol* (2000), 83: 3570-3574).

Delta receptors are involved in the migraine mechanism (Charles & Pradhan, *Curr Opin* (2016), 29: 314-319).

Indeed, delta agonists (e.g. SNC80) inhibit the hyperalgesia related to migraine in mice (Pradhan et al., *Br J Pharmacol* (2014), 171: 2375-2384).

In cases of trigeminal nerve neuropathy, continuous activation of endogenous opioid neurotransmission has been demonstrated, occurring mainly by activation of mu receptors (Da Silva et al., *Curr Pain Headache Rep* (2014), 18: 429. doi: 10.1007/s11916-014-0429-0). In the same way, an increase of met-ENK has been observed in migraine patients (Mosnaim et al., *Headache* (1986), 26: 278-281).

In cases of migraine, mu receptors modulate nociceptive signals (Storer et al., *Br J Pharmacol* (2003), 138: 317-324). Indeed, it was demonstrated that a mutation of the mu receptor gene increased sensitivity to migraine attacks (Menon et al., *Pain* (2012), 13: 513-519). A peripheral mu agonist action has also been demonstrated (Baillie et al., *Neuropharmacol* (2015), 93: 267-273).

Opioids (morphine, codeine and pethidine) are effective in migraine (Siberstein, *Cephalalgia* (2000), 20: 854-864). In fact, it has been demonstrated that opioid agonists inhibit neurogenic meningeal vasodilatation (Williamson et al., *Br J Pharmacol* (2001), 133: 807-814), as do triptans.

Transfer by means of herpes simplex virus type-1 (HSV-1) permits overexpression of pro-enkephalins in primary sensory neurons in the lumbar region. Such an administration showed an anti-hyperalgesic effect in a chronic pain model in rats or in a neuropathic model resulting from spinal nerve ligature (Hao et al., *Pain* (2003), 102: 135-142). Unlike morphine, this type of treatment did not show tolerance after 4 weeks of treatment or after 8 weeks of treatment (Hao et al., *Pain* (2003), 102: 135-142). In contrast, resistance was observed during morphine treatment (Meunier et al., *Mol Therap* (2005), 11: 608-616).

There is therefore a need for preventative therapy and improved treatments for trigeminal nerve pains, especially migraines, or trigeminal neuralgia, which avoid the side effects of known treatments, in particular the phenomena of addiction and habituation. In cases of chronic migraine, for example, with a preventive medication, the frequency of migraines may be reduced and the acute treatment response improved, which reduces healthcare costs and the number of lost work days and improves patient quality of life.

SUMMARY

Mixed inhibitors of enzymatic degradation of endogenous enkephalins have made it possible to completely reveal the pharmacological activities and, in particular, the analgesic and antidepressant activities of enkephalins. Different series of mixed inhibitors have been described in different patents (WO 98/18803; WO 2009/138436; WO 2010/010106; WO 2014/064166).

Good antinociceptive efficacy was demonstrated in numerous acute or neuropathic pain models (Poras et al., *J Med Chem* (2014), 57: 5748-5763; Bonnard et al., *Pharma Res Per* (2015), 3(2), e00116, doi: 10.1002/prp2.116; Poras et al., *Eur J Med Chem* (2015), 102: 58-67). However, the use of these compounds as analgesics acting on pains specifically relating to the trigeminal nerve, such as migraine or trigeminal neuralgia, has never been described or suggested.

However, surprisingly, the inventors have demonstrated that amino acid derivatives containing a disulfanyl group, described as mixed NEP and APN inhibitors and having analgesic activities in central or peripheral pain models after intravenous or oral administration, are effective for the prevention and treatment of pains related to the trigeminal nerve, especially for migraines treatment, whether chronic or acute.

According to another embodiment, amino acid derivatives containing a disulfanyl group according to the invention are effective in the treatment and prevention of migraine attacks.

Unlike the method involving transfer using herpes simplex virus type-1 (HSV-1) cited previously, an overexpression of enkephalin within the nervous system is not sought via the use of these mixed NEP and APN inhibitors.

The invention therefore relates to a pharmaceutically-acceptable salt of a compound of formula (I) to prevent or treat trigeminal nerve pains, in particular migraines or trigeminal neuralgia:

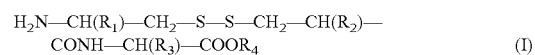

$$H_2N-CH(R_1)-CH_2-S-S-CH_2-CH(R_2)-CONH-CH(R_3)-COOR_4 \quad (I)$$

wherein:
$R_1$ represents:
 a saturated or unsaturated, linear or branched hydrocarbon chain, containing 1 to 6 carbon atoms, optionally substituted by:
  an OR, SR or S(O)R radical, in each of these radicals, R represents a hydrogen, a linear or branched hydrocarbon chain of 1 to 4 carbon atoms, a phenyl or benzyl radical,
  a phenyl or benzyl radical,
 a phenyl or benzyl radical optionally substituted by:
  1 to 5 halogen atoms, notably fluorine,
  an OR, SR or S(O)R radical, R having the same meaning as previously in each of these radicals,
  a methylene radical substituted by a 5 or 6 atom heterocycle, aromatic or saturated, having a nitrogen or sulfur atom as heteroatom, optionally oxidized in the form of N-oxide or S-oxide;
$R_2$ represents:
 a phenyl or benzyl radical optionally substituted by:
  1 to 5 halogens, notably fluorine,
  an OR or SR radical, R having the same meaning as previously in each of these radicals,
  an amino group, optionally mono- or disubstituted by a cyclic or linear aliphatic group, of 1 to 6 carbon atoms,
  a 5 or 6 atom aromatic ring,
  an aromatic heterocycle with 5 to 6 atoms, the heteroatom being an oxygen, nitrogen or sulfur,
  a methylene group substituted by a 5 or 6 atom heterocycle, aromatic or saturated, the heteroatom being an oxygen, nitrogen or sulfur, the nitrogen and sulfur atoms optionally being oxidized in the form of N-oxide or S-oxide;
$R_3$ represents:
 a hydrogen,
 an OH or OR group, R having the same meaning as previously,
 a saturated hydrocarbon (alkyl) chain, linear or branched, having 1 to 6 carbon atoms, optionally substituted by an OR or SR radical, in each of these radicals, R has the same meaning as previously,
 a phenyl or benzyl radical optionally substituted by:
  1 to 5 halogens, notably fluorine,
  an OR or SR group, R having the same meaning as previously, and
$OR_4$ represents:
 a glycolate $OCH_2COOR'$ or lactate $OCH(CH_3)COOR'$ radical, in each of these radicals, R □represents:

a saturated hydrocarbon chain (alkyl) with 1 to 6 carbon atoms, linear or branched, optionally substituted by a $C_1$-$C_3$ alkoxy group, preferably a $C_1$-$C_4$ alkyl group optionally substituted by a methoxy group, a $C_5$-$C_8$, cycloalkyl group, preferably a $C_5$-$C_6$ cycloalkyl group, a phenyl, benzyl, heteroaryl or alkyl heteroaryl group;

an OCH(R")O(CO)OR' or OCH(R")O(CO)R' group, in each of these radicals, R □has the same meaning as previously and R" represents:

a hydrogen atom, a linear or branched $C_1$-$C_6$ alkyl chain optionally substituted by a $C_1$-$C_3$ alkoxy group, preferably a $C_1$-$C_4$ alkyl group optionally substituted by a methoxy group, a $C_5$-$C_8$, cycloalkyl group, preferably a $C_5$-$C_6$ cycloalkyl group, a phenyl, benzyl, heteroaryl or alkyl heteroaryl group;

an OCH(CH$_2$OCOR')$_2$ or OCH$_2$—CH(OCOR')—CH$_2$OCOR' triglyceride radical, R' having the same meaning in each of these radicals;

a glycoside radical such as D-glucose, β-D-glucopyranose, α- or β-galactopyranose;

a sulfonate OCH$_2$CH$_2$(SO$_2$)CH$_3$ radical;

an OCH(CH$_2$OH)$_2$ radical.

The present invention also relates to a composition, notably for its use to prevent or relieve (treat) trigeminal nerve pains, said composition comprising as active ingredient at least one pharmaceutically-acceptable salt of a compound of formula (I) of the invention, and at least one pharmaceutically-acceptable excipient.

The present invention also relates to a composition, notably for its use to prevent migraine attacks, said composition comprising as active ingredient at least one pharmaceutically-acceptable salt of a compound of formula (I) of the invention, and at least one pharmaceutically-acceptable excipient.

The present invention also relates to a pharmaceutically-acceptable salt of a compound of formula (I), or a composition containing it, for the production of a medication to prevent or relieve (treat) trigeminal nerve pains, in particular migraine or trigeminal neuralgia.

The present invention also relates to the use of a pharmaceutically-acceptable salt of a compound of formula (I), or a compound containing it, for the production of a drug to prevent migraine attacks.

The present invention also relates to a method for preventing or treating trigeminal nerve pains, in particular migraines or trigeminal neuralgia, comprising the administration of an effective dose of a pharmaceutically-acceptable salt of a compound of formula (I), or a composition comprising it, to a patient in need thereof.

The present invention also relates to a method for preventing migraines attacks comprising the administration of an effective dose of a pharmaceutically-acceptable salt of a compound of formula (I), or a composition comprising it, to a patient in need thereof.

The present invention also relates to a composition comprising a quantity comprised between 50 mg and 800 mg, of a salt of a compound of formula (I) or a salt of formula (II).

In the present invention, the patient (suffering from trigeminal nerve pains, in particular migraine attacks) is typically an animal, preferably a mammal, advantageously it is a human.

DETAILED DESCRIPTION

Figure 1:
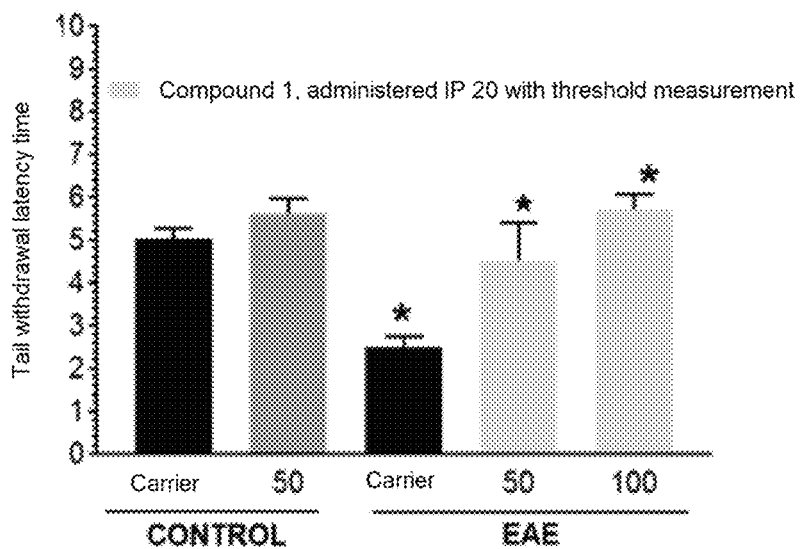
FIG. 1 is a graph showing the comparative tail withdrawal latency time (in seconds) for a control group (with carrier or 20 minutes after IP injection of a dose of 50 mg/kg of compound 1), and the EAE model group (with carrier or after 30 minutes after injection of a dose of 50 mg/kg or 100 mg/kg of compound 1)

In the context of the present invention "trigeminal nerve pain" means pain relating to the sensory part of the trigeminal. "Pain relating to the sensory part of the trigeminal", according to the present invention, covers different types of pain originating from the sensory part of the trigeminal nerve. In particular, it is a question of craniofacial pain, and especially orofacial pain. It can also be pain located in the cornea, meninges or dental pulp, the dermatomas of the face, mucosal tissues, vascular tissues or muscle tissues. It may also be pain located in the cornea, conjunctiva, nose, intranasal mucosa, eyelids, supraorbital skin, forehead, scalp, lips, jaw, tongue, gums or oral mucosa.

In particular, it is a migraine or trigeminal neuralgia, especially essential trigeminal neuralgia and symptomatic trigeminal neuralgia. It may also be headaches, especially acute headaches, in particular recurrent, or their symptoms such as cephalic cutaneous allodynia. It may also be peripheral trigeminal pain associated with multiple sclerosis.

In the context of the present invention, the term "migraine" refers to both acute migraine, which defines an occasional headache lasting 4 to 72 hours occurring less than 15 days a month, and chronic migraine, which is characterized by chronic headaches, with headaches that recur repeatedly either for no apparent reason, or following exposure of the patient to a triggering factor (such as bright light, menstruation, etc.) fifteen days or more a month (Headache Classification Committee of the International Headache Society (IHS). The International Classification of Headache Disorders, 3rd edition, *Cephalalgia* (2013), 33: 629-808).

In the context of the present invention, the terms "migraine attacks" or "chronic migraine" are interchangeable.

In the sense of the present invention, treatment means the attenuation or resolution of pain. In this case, the compound or composition according to the invention is administered after onset of pain.

In the sense of the present invention, prevention means that the pain has not started and the compound or composition according to the invention is administered before the onset of pain, thereby preventing said onset of pain or attenuating future pain.

In the sense of the present invention, "therapeutic dose" means the daily quantity of active ingredient (for example salt of the compound of formula (I)) administered to the patient having need thereof.

"Repeatedly" means that the therapeutic dose or compositions of the invention, as applicable, are administered by administrations staggered over time for a period ranging from several days to several months, most often with regular time intervals between administrations.

In the sense of the present invention, "amino" group means a group of formula —NR*R**, where R* and R** represent, independently of one another, a hydrogen atom or a saturated or unsaturated, linear, branched or cyclic hydrocarbon group containing 1 to 6, preferably 1 to 4, carbon atoms, or R* and R** form together, with the nitrogen atom which carries them, a 5- or 6-membered heterocycle, saturated or unsaturated, and having no other heteroatom other than the nitrogen which carries both the R* and R** radicals. In particular, the amino group may be an —NH$_2$, —NHMe, —NHEt, —NHPr, NHiPr, —NHBu, —NHiBu, —NHtBu, piperidinyl or pyrrolidinyl group. Preferably, an amino group is a group of the formula —NR*R**, where R* and R** represent, independently of one another, a hydrogen atom or a linear or branched $C_1$-$C_6$ alkyl group (preferably $C_1$-$C_4$).

In the context of the present invention, the term "hydrocarbon chain" designates alkanes, alkenes or alkynes. In particular, the expression "saturated hydrocarbon chain" designates alkyl radicals with 1 to 6 carbon atoms ($C_1$-$C_6$) or 1 to 4 carbon atoms ($C_1$-$C_4$), linear or branched. Examples of alkyl radicals having 1 to 4 carbon atoms include methyl, ethyl, propyl, butyl, isopropyl, 1-methylethyl, 1-methyl-propyl and 2-methyl-propyl radicals. Examples of alkyl radicals having 1 to 6 carbon atoms include pentyl, hexyl 1-methyl-butyl, 1-methyl-pentyl 2-methyl-butyl 2-methyl-pentyl, 3-methyl-butyl, 3-methyl-pentyl, 4-methyl-pentyl or 1-ethyl-propyl, 1-ethyl-butyl, 2-ethyl-butyl radicals. The expression "unsaturated hydrocarbon chain" designates alkenyl radicals (at least one double bond), for example vinyl, allyl or the like, or alkynyl radicals (at least one triple bond) containing 2 to 6 carbon atoms, or 2 to 4 carbon atoms, linear or branched.

In the sense of the present invention, "cycloalkyl" means a saturated hydrocarbon ring containing 5 to 8 carbon atoms, in particular the cyclohexyl, cyclopentyl or cycloheptyl group.

The term "halogen" used here designates a chlorine, a bromine, an iodine and a fluorine. Advantageously, it is a fluorine, bromine or chlorine atom. More advantageously, it is a fluorine or bromine atom, and preferably fluorine.

In the sense of the present invention, "aromatic" means an aromatic group, preferably containing 5 to 10 carbon atoms, unless otherwise stated, and comprising one or more fused rings, such as, for example, a phenyl or naphthyl group. Advantageously it is phenyl.

In the sense of the present invention, "heteroaromatic" group or radical means any aromatic group as defined above in which one or more carbon atoms have been replaced by one or more heteroatoms, advantageously 1 to 4 and even more advantageously 1 to 2, such as, for example, sulfur, nitrogen or oxygen atoms, the sulfur and nitrogen atoms possibly being oxidized in the form of S-oxide or N-oxide. Examples of heteroaromatic groups are furyl, thienyl, pyrrolyl, pyridinyl, pyrimidyl, pyrazolyl, imidazolyl, tetrazolyl or indyl groups. Preferably, it is a thienyl group. In the sense of the present invention, "heteroaromatic ring with 5 or 6 atoms" means a heteroaromatic group such as defined above comprising only a single 5- or 6-atom ring. This is particularly a thienyl, pyrrolyl, pyridinyl, pyrimidyl, pyrazolyl, imidazolyl or tetrazolyl group.

In the sense of the present invention, "heterocycle" means a hydrocarbon ring advantageously with 5 or 6 atoms, of which one or more carbon atoms have been replaced by one or more heteroatoms, advantageously 1 to 4 and even more advantageously 1 to 2, such as, for example, sulfur, nitrogen or oxygen atoms, the sulfur and nitrogen atoms possibly being oxidized in the form of S-oxide or N-oxide. Unless otherwise stated, this ring may be saturated or aromatic. Examples of aromatic or saturated 5- or 6-membered heterocyclic rings having a nitrogen or sulfur atom as the heteroatom include, but are not limited to, the following radicals: thienyl, pyrrolyl, imidazolyl, pyrazolyl, isothiazolyl, pyridyl, pyrazinyl, pyrimidinyl, pyridazinyl, pyrrolidinyl, pyrrolinyl, imidazolidinyl, pyrazolidinyl, pyrazolinyl, piperidyl, piperazinyl, thiadiazolyl, the nitrogen and sulfur atoms being optionally oxidized in the form of N-oxide or S-oxide. Examples of heterocyclic rings with 5 or 6 atoms, aromatic or saturated, having an oxygen atom as the heteroatom include, but are not limited to, the following radicals: furyl, pyranyl, isoxazolyl, morpholinyl, furazanyl, oxazolyl, oxazolidinyl, oxazolinyl.

Compounds of formula (I) potentially have 2 to 9 asymmetric centers. The radicals $R_1$, $R_2$ and $R_3$ are typically introduced so as to obtain optically pure sequences corresponding to a stereochemistry recognized by enzymatic activities. $R_4$ radicals may optionally contain an unresolved asymmetric center.

Compounds of the invention are in the form of pharmaceutically-acceptable salts, or a hydrate thereof. In the present invention, "pharmaceutically acceptable" means something usable in the preparation of a pharmaceutical composition that is generally safe, nontoxic and neither biologically or otherwise undesirable and which is acceptable for veterinary use as well as a human pharmaceutical.

"Pharmaceutically-acceptable salts" of a compound means salts that are pharmaceutically acceptable, as defined here, and which have the desired pharmacological activity of a parent compound. Such salts include:

(1) pharmaceutically-acceptable acid addition salts formed with acids, and (2) hydrates and solvates thereof.

Typically, compounds of formula (I) are in the form of addition salts obtained with pharmacologically-acceptable organic or mineral acids such as phosphates, hydrochloride, acetate, methanesulfonate, borate, lactate, fumarate, succinate, hemisuccinate, citrate, tartrate, hemitartrate, maleate, ascorbate, hemifumarate, hexanoate, heptanoate, hippurate, hydrocinnamate, phenylglyoxylate and nicotinate.

The solvate is preferably an alcoholate, such as an ethanolate.

Preferably, the compounds of the invention are in the form of fumarate salts, or a hydrate thereof.

Radical $R_1$ advantageously represents an alkyl radical with 1 to 6 or 1 to 4 carbon atoms, optionally substituted by an OR, SR or S(O)R, radical, in each of these radicals, R has the same meaning as previously, and advantageously represents a hydrogen, a linear or branched hydrocarbon chain of 1 to 4 carbons, a phenyl or benzyl radical. $R_1$ still more advantageously represents an alkyl radical having 1 to 4 carbon atoms substituted by an SR radical, R having the same meaning as previously, in particular, R represents a saturated linear or branched hydrocarbon chain of 1 to 4 carbon atoms.

$R_2$ advantageously represents:
a phenyl or benzyl group optionally substituted by:
  1 to 5 halogen atoms, notably fluorine, a hydroxyl or a thiol, an ether OR or a thioether SR, R having the same meaning as above,
  an aromatic ring or aromatic heterocycle with 5 to 6 atoms, the heteroatom being an oxygen, nitrogen or sulfur,
  a methylene group substituted by a 5 or 6 atom heterocycle, aromatic or saturated, the heteroatom being an oxygen, nitrogen or sulfur, the nitrogen or sulfur atoms optionally being oxidized in the form of N-oxide or S-oxide;

In particular, radical $R_2$ represents a benzyl or phenyl radical, or a methylene radical substituted by a 5 or 6 atom heterocycle, aromatic or saturated, having nitrogen or sulfur as heteroatom, optionally oxidized in the form of N-oxide or S-oxide; In particular, radical $R_2$ represents a benzyl or methylene radical substituted by a 5 or 6 atom heterocycle, aromatic or saturated, having nitrogen or sulfur as heteroatom, optionally oxidized in the form of N-oxide or S-oxide, still more advantageously a benzyl radical or a methylene radical substituted by a thiophenyl radical (thienyl).

Advantageously, radical $R_3$ represents:
a hydrogen,
an OH or OR group, R having the same meaning as above,
a linear or branched $C_1$-$C_6$ alkyl, optionally substituted by an OH, OR, SH or SR group, R having the same meaning as above,
a phenyl or benzyl group, optionally substituted by 1 to 5 halogens, notably fluorine or by an OR or SR group, R having the same meaning as above.

In particular, radical $R_3$ represents a hydrogen atom or an alkyl radical with 1 to 6 carbon atoms, still more advantageously 1 to 4 carbon atoms, optionally substituted by an OR or SR radical, in each of these radicals, R has the same meaning as previously. Even more advantageously, radical $R_3$ represents a hydrogen atom or an alkyl radical with 1 to 6 carbon atoms, still more advantageously 1 to 4 carbon atoms, substituted by an OH or SH radical.

Radical $OR_4$ advantageously represents:
a glycolate $OCH_2COOR'$ radical, R' having the same meaning as previously (in particular R' represents a $C_1$-$C_4$ alkyl group optionally substituted by a methoxy group or a $C_5$-$C_6$ cycloalkyl group,
an $OCH(R'')O(CO)OR'$ or $OCH(R'')O(CO)R'$ radical, R' and R'' having the same meaning as previously (in particular R □ and/or R'' represent a $C_1$-$C_4$ alkyl group optionally substituted by a methoxy group or a $C_5$-$C_6$ cycloalkyl group where R'' is a hydrogen atom),
an $OCH(CH_2OCOR')_2$ or $OCH_2$—$CH(OCOR')$—$CH_2OCOR'$ triglyceride radical, in each of these radicals, R' having the same meaning as previously
a glycoside radical such as D-glucose,
an $OCH_2CH_2(SO_2)CH_3$ sulfonate radical;
an $OCH(CH_2OH)_2$ radical
Alternatively, radical $OR_4$ may represent:
a glycolate $OCH_2COOR'$ or lactate $OCH(CH_3)COOR'$ radical;
an $OCH_2OCOR'$ or $OCH(CH_3)OCOOR'$ group, or
an $OCH(CH_2OCOR')_2$ or $OCH_2$—$CH(OCOR')$—$CH_2OCOR'$ triglyceride radical,
R' representing a linear or branched $C_1$-$C_4$ alkyl group.

In particular, radical $OR_4$ represents an $OCH(R'')O(CO)OR'$ or $OCH(R'')O(CO)R'$ group, radical R' representing a $C_1$-$C_4$ alkyl chain (in particular the ethyl radical) and radical R'' representing a methyl, $CH(CH_3)_2$, cyclohexyl or phenyl radical.

According to one particular embodiment, the salt of the invention is a salt of formula (II):

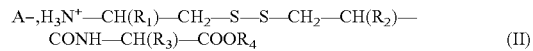

$$A-, H_3N^+\text{—}CH(R_1)\text{—}CH_2\text{—}S\text{—}S\text{—}CH_2\text{—}CH(R_2)\text{—}CONH\text{—}CH(R_3)\text{—}COOR_4 \qquad (II)$$

wherein:
A− represents a phosphate, chloride, acetate, methanesulfonate, borate, lactate, fumarate, succinate, hemisuccinate, citrate, tartrate, hemi-tartrate, maleate, ascorbate, hemifumarate, hexanoate, heptanoate, hippurate, hydrocinnamate, phenylglyoxylate or nicotinate anion;
$R_1$ represents a saturated or unsaturated, linear or branched hydrocarbon chain, containing 1 to 6 carbon atoms, optionally substituted by an OR, SR or S(O)R group in which R represents a hydrogen, a linear or branched hydrocarbon chain of 1-4 carbons, a phenyl or benzyl radical;
$R_2$ represents:
a phenyl or benzyl group optionally substituted by:
  1 to 5 halogen atoms, notably fluorine, a hydroxyl or a thiol, an ether OR or a thioether SR, R having the same meaning as above,
  an aromatic ring or aromatic heterocycle with 5 to 6 atoms, the heteroatom being an oxygen, nitrogen or sulfur,
  a methylene group substituted by a 5 or 6 atom heterocycle, aromatic or saturated, the heteroatom being an oxygen, nitrogen or sulfur, the nitrogen or sulfur atoms optionally being oxidized in the form of N-oxide or S-oxide;
$R_3$ represents:
a hydrogen,
an OH or OR group, R having the same meaning as above,
a linear or branched $C_1$-$C_6$ alkyl, optionally substituted by an OH, OR, SH or SR group, R having the same meaning as above,
a phenyl or benzyl group, optionally substituted by 1 to 5 halogens, notably fluorine or by an OR or SR group, R having the same meaning as above;
$OR_4$ represents:
a glycolate $OCH_2COOR'$ or lactate $OCH(CH_3)COOR'$ radical;
an $OCH_2OCOR'$ or $OCH(CH_3)OCOOR'$ group, or
an $OCH(CH_2OCOR')_2$ or $OCH_2$—$CH(OCOR')$—$CH_2OCOR'$ triglyceride radical,
R' representing a linear or branched $C_1$-$C_4$ alkyl.

Preferably, in formula (II), A− represents a fumarate anion.

All the combinations of particular, advantageous and preferred embodiments of substituents $R_1$, $R_2$, $R_3$ and $R_4$ in formulas I and II are envisaged in the present invention.

In particular, the invention concerns the acid addition salts of the following compounds, in particular fumarate salts thereof:

1-(2-(1-(2,3-diacetoxypropoxycarbonyl)-ethylcarbamoyl)-3-thiophen-3-ylpropyl disulfanylmethyl)-3-methylsulfanylpropyl-amine, 1-(2-(1-(2-methanesulfonylethoxycarbonyl)-ethylcarbamoyl)-3-thiophen-3-ylpropyl disulfanylmethyl)-3-methylsulfanylpropyl-amine, 1-(2-(1-(1-ethoxycarbonyloxyethoxycarbonyl))-ethylcarbamoyl)-3-thiophen-3-yl-propyl disulfanylmethyl)-3-methylsulfanylpropyl-amine, 1-(2-(1-ethoxycarbonylmethyloxycarbonylethylcarbamoyl)-3-thiophen-3-yl-propyl disulfanylmethyl)-3-methylsulfanylpropyl-amine, 1-(2-(1-(1-ethoxycarbonyloxyethoxycarbonyl)-2-hydroxypropylcarbamoyl)-3-thiophen-3-ylpropyldisulfanylmethyl)-3-methylsulfanylpropyl-amine, 1-(2-(1-(2-acetoxy-1-acetoxymethylethoxycarbonyl)-ethylcarbamoyl)-3-thiophen-3-yl propyldisulfanylmethyl)-3-methylsulfanylpropyl-amine, 1-(2-(1-(2-hydroxy-1-hydroxymethylethoxycarbonyl)-ethylcarbamoyl)-3-thiophen-3-yl propyldisulfanylmethyl)-3-methylsulfanylpropyl-amine, 1-(2-(1-(3,4,5,6-tetrahydroxytetrahydropyran-2-ylmethoxycarbonyl)-ethylcarbamoyl)-3-thiophen-3-yl-propyldisulfanylmethyl)-3-methylsulfanylpropyl-amine, 1-(2-(1-(1-ethoxycarbonyloxy-ethoxycarbonyl)-2-hydroxypropylcarbamoyl)-3-phenyl propyldisulfanylmethyl)-3-methylsulfanylpropyl-amine, 1-(2-(1-(2-acetoxy-1-acetoxymethyl-ethoxycarbonyl)-2-hydroxypropylcarbamoyl)-3-phenylpropyldisulfanylmethyl)-3-methylsulfanylpropyl-amine, 1-(2-((1-ethoxycarbonyloxy-ethoxycarbonylmethyl)-carbamoyl)-3-phenyl-propyl disulfanylmethyl)-3-methylsulfanylpropyl-amine, 3-(2-amino-4-methylsulfanyl-butyldisulfanyl)-2-benzyl-N-(5-ethyl-(1,3,4)-thiadiazol-2-yl)-propionamide, 1-(2-((1-ethoxycarbonyloxy-2-methyl-propoxycarbonylmethyl)-carbamoyl)-3-phenyl-propyldisulfanylmethyl)-3-methylsulfanyl-propyl-amine, 1-(2-((cyclohexyl-ethoxycarbonyloxy-methoxycarbonylmethyl)-carbamoyl)-3-phenyl-propyldisulfanylmethyl)-3-methylsulfanyl-propyl-amine, 1-(2-((ethoxycarbonyloxy-phenyl-methoxycarbonylmethyl)-carbamoyl)-3-phenyl-propyldisulfanylmethyl)-3-methylsulfanyl-propyl-amine, 3-methylsulfanyl-1-(3-phenyl-2-((1-propionyloxy-ethoxycarbonylmethyl)-carbamoyl)-propyldisulfanylmethyl)-propyl-amine, 1-(2-((2-methyl-1-propionyloxy-propoxycarbonylmethyl)-carbamoyl)-3-phenyl-propyldisulfanylmethyl)-3-methylsulfanyl-propyl-amine, 1-(2-((cyclohexyl-propionyloxy-methoxycarbonylmethyl)-carbamoyl)-3-phenyl-propyldisulfanylmethyl)-3-methylsulfanyl-propyl-amine, 3-methylsulfanyl-1-(3-phenyl-2-((phenyl-propionyloxymethoxycarbonylmethyl)-carbamoyl)-propyl disulfanylmethyl)-propyl-amine.

Preferably, the compound of the invention is (5S, 10S)-10-benzyl-16-methyl-11,14,18-trioxo-15,17,19-trioxa-2,7,8-trithia-12-azahenicosan-5-aminium fumarate (or (E)-3-carboxyacrylate) (hereinafter compound 1):

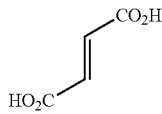

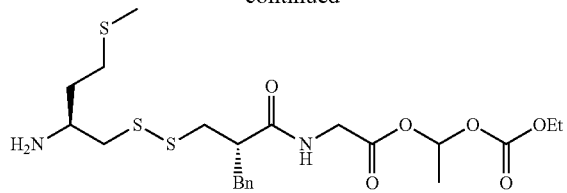

Salts of compounds of formula (I) may be synthesized, for example, by methods described in WO 2007/048787. More particularly, compound 1 may be synthesized as described in WO 2017/064250.

Compounds of formula (I) are formulated in accordance with the methods described by the person skilled in the art for the desired administration route.

The invention also relates to pharmaceutical compositions containing as active ingredient at least one pharmaceutically acceptable salt of a compound of general formula (I) or hydrates of these salts in combination with one or more inert carriers or other pharmaceutically-acceptable carriers, for use in preventing or relieving trigeminal nerve pains, particularly migraines or trigeminal neuralgia.

Pharmaceutical compounds according to the invention may be, for example, compositions that can be administered orally, nasally (aerosol administration), sublingually (administration by perlingual diffusion), rectally, parenterally, intravenously and percutaneously. Examples of compounds that can be administered orally include tablets, capsules, granules, microspheres, powders and oral solutions or suspensions. In particular, they are soluble in alcohol/polysorbate/water solvents, in particular ethanol/Tween®/water and mannitol/water or by means of cyclodextrins suitable for administration in humans, which are frequently used for intravenous administration. Compositions according to the invention may therefore be administered intravenously. They may also be administered orally or nasally, in particular via an aerosol or by perlingual diffusion or in an appropriate galenic preparation (microemulsions).

Compositions according to the invention may be administered either in the aerosol (microemulsion) form orally or nasally or administered intravenously. These administration routes also permit the composition according to the invention to be administered by a non-digestive route. This is particularly interesting when the composition comprises additional compounds, which may have adverse effects on the digestive system (in particular the intestine), such as, for example, cannabinoid derivatives. This also permits increasing the bioavailability (especially cerebral) of compounds or associations Preferably, compositions of the invention are appropriate for oral administration or intravenous administration.

In one particular embodiment, a formulation of the present invention comprises a cyclodextrin, such as hydroxypropyl beta-cyclodextrin or sulfobutyl ether beta-cyclodextrin, or sodium polystyrene sulfonate.

Compositions administered in accordance with the methods described in the present invention contain an active quantity for use, of a salt of a compound of formula (I) or a salt of formula (II), in particular of compound 1. This means a sufficient quantity to prevent or relieve (treat) trigeminal nerve pains, in particular migraines, trigeminal neuralgia, cluster headaches or peripheral trigeminal pains related to multiple sclerosis.

The therapeutic dose of a compound of the invention varies depending on numerous parameters such as, for example, the administration route chosen, weight, age, sex, advanced state of the disease to be treated and the sensitivity of the individual to be treated. Consequently, the optimum dosage will be determined, depending on the parameters deemed relevant, by the specialist in the case.

According to the examples of the present invention, the administration of a daily dose of 4000 mg for 5 consecutive days did not cause the appearance of adverse side effects. The treatment may therefore be administered for several days without risk of toxicity.

Advantageously, the compositions according to the invention, for their use to prevent or treat trigeminal nerve pains, in particular migraines and trigeminal neuralgia, may include a second active ingredient already known for pain prevention and treatment.

Another object of the invention is a kit comprising:
  i) A first composition comprising at least one compound of formula (I) such as defined previously, and
  ii) A second composition comprising at least a second active ingredient useful to prevent or treat trigeminal nerve pains as a combination product for simultaneous, separate or staggered use.

According to one embodiment, the pharmaceutically-acceptable salt of a compound of formula (I) or a salt of formula (II) according to the invention, in particular compound 1, is used for the prevention of migraine attacks.

The prevention of chronic migraines by the pharmaceutically-acceptable salt of a compound of formula (I) or of a salt of formula (II) according to the invention, in particular of compound 1, is particularly suitable for patients sensitive to migraines, whose headaches recur periodically or are caused by a specific factor such as fatigue, stress, menstruation, bright or artificial light (during long exposure to screens for example), noise, some odors, certain foods (alcohol). The pharmaceutically acceptable salt of a compound of formula (I) may also be used preventively during the appearance of warning signs of a migraine attack such as an aura, a visual disorder which may manifest itself in the form of a dark spot surrounded by a glittering halo, geometric lines, bright spots in half the field of vision, visual field loss, double vision or the temporary loss of vision of one or both eyes. The patient will have identified the risks factors that are highly likely to induce migraines for them from experience.

According to one embodiment, the pharmaceutical compositions according to the invention are used for preventing migraine attacks, in particular migraine attacks triggered by a specific risk factor such as described above.

Thus, preferably, the pharmaceutical compositions used to prevent migraine attacks are administered orally. Advantageously, these compositions are administered repeatedly.

Advantageously, a therapeutic dose of a salt of a compound of formula (I) or a salt of formula (II), in particular compound 1 such as described above is administered to a patient in order to prevent migraine attacks. Preferably, said dose is administered for preventing migraine attacks in patients sensitive to migraine attacks as described above. Thus, for preventing migraine attacks, the therapeutic dose is administered before the onset of pain and/or before exposure to a specific migraine trigger factor. For example, a women who regularly has migraines during her menstrual period could take the therapeutic dose one to several days before the start of her period.

Preferably, in order to prevent migraine attacks, the therapeutic dose administered to the patient in need thereof is administered repeatedly. Advantageously, the therapeutic dose is administered for preventing migraine attacks orally or parenterally, advantageously orally, in particular in galenic form.

The compositions of the invention may advantageously comprise a second active ingredient useful for preventing migraine attacks, in particular beta blockers, antidepressants, anticonvulsants, calcium channel blockers, and/or CGRP inhibitors.

Thus, in order to prevent migraine attacks, the composition also comprises a beta blocker, such as atenolol, metoprolol, nadolol, propranolol and/or timolol. Antidepressants may be selected from amitriptyline, doxepin, nortriptyline, protriptyline and/or venlafaxine. Anticonvulsants may be selected from carbamazepine, gabapentin, topiramate and/or valproate/divalproex. Calcium channel blockers may be selected from verapamil, dihydropyridines and/or flunarizine. CGRP (calcitonin gene-related peptide) inhibitors are described in Tso A R et al., *Curr Treat Options Neurol* (2017), 19: 27 DOI 10.1007/s11940-017-0463-4 "*Anti-CGRP monoclonal antibodies: the next era of migraine prevention?*" whose content is incorporated here for reference.

According to one particular embodiment, the composition of the invention used to prevent migraine attacks, also comprises a second active ingredient selected from beta blockers, antidepressants, calcium channel blockers and/or CGRP inhibitors; advantageously the second active ingredient is selected from propranolol, topiramate or amitriptyline.

Another object of the invention is a kit comprising:
  i) a first composition comprising at least one compound of formula (I) such as defined previously, and
  ii) a second composition comprising at least one second active ingredient useful for preventing migraine attacks, notably selected from beta blockers, antidepressants, anticonvulsants, calcium channel blockers and/or CGRP inhibitors, advantageously the second active ingredient is selected from propranolol, topiramate or amitriptyline, as combination products for simultaneous, separate or staggered use.

This kit may be used as a drug, notably in the prevention of migraine attacks.

According to another embodiment, the pharmaceutically-acceptable salt of a compound of formula (I) or a salt of formula (II) according to the invention, in particular compound 1, is used for the treatment of trigeminal nerve pains, especially migraines or trigeminal neuralgia.

Advantageously, according to the preceding embodiment, the pharmaceutically-acceptable salt of a compound of formula (I) or a salt of formula (II) according to the invention, in particular compound 1, is used for the treatment of acute migraines.

According to one embodiment, the pharmaceutical compositions according to the invention are used for the treatment of trigeminal nerve pains, notably migraines or trigeminal neuralgia, in particular acute migraines. According to one embodiment, a therapeutic dose of a salt of a compound of formula (I) or a salt of formula (II), in particular compound 1 such as described above is administered to a patient in order to treat trigeminal nerve pains. In particular, this dose is administered to a patient in order to treat migraines, for example acute migraines.

According to the preceding embodiment, the therapeutic dose to treat trigeminal nerve pains, especially migraines or trigeminal neuralgia, in particular acute migraines, is administered to the patient when the pain occurs. In the case of acute pain, this dose is generally effective, i.e. a single therapeutic dose is sufficient to attenuate or resolve the pain.

Advantageously, in order to treat trigeminal nerve pain, in particular migraines or trigeminal neuralgia, the therapeutic dose of a salt of a compound of formula (I) or a salt of formula (II), in particular compound 1, administered to the patient in need thereof is comprised between 200 and 800 mg.

Preferably, in order to treat trigeminal nerve pains, particularly migraines, the therapeutic dose such as described above is administered in one to four administrations. This therapeutic dose may advantageously be administered parenterally or orally.

According to another embodiment, the compositions of the invention may advantageously comprise a second active ingredient useful to treat trigeminal nerve pains, in particular migraine, especially acute migraine, chosen from among analgesics, nonsteroidal antiinflammatories (NSAIDs), opioids, triptans, GABA modulators, Nav1.7 sodium channel blockers, CGRP inhibitors and/or cannabinoids, without this being limiting.

Thus, according to one embodiment, the composition to treat trigeminal nerve pains, in particular migraines, especially acute migraines, also comprises an analgesic, especially NSAIDs, aspirin and acetaminophen.

According to another embodiment, the composition to treat trigeminal nerve pains, in particular migraines, especially acute migraines, also comprises an NSAID, such as ibuprofen, diclofenac, piroxicam, ketoprofen, indomethacin, acetylsalicylic acid, celecoxib, naproxen.

According to another embodiment, the composition to treat trigeminal nerve pain, in particular migraines, especially acute migraines, also comprises an opioid, especially alfentanil, anileridine, buprenorphine, butorphanol, carfentanil, codeine, dextropropoxyphene, fentanyl, hydrocodone, hydromorphone, morphine, nalbuphine, oxycodone, oxymorphone, pentazocine, meperidine, propoxyphene, remifentanil, sufentanil, and tramadol. Advantageously, it is morphine or one of its derivatives, especially morphine. Indeed, morphine is also able to potentiate the analgesic effect induced by the compounds according to the invention.

According to another embodiment, the composition to treat trigeminal nerve pains, in particular migraines, especially acute migraines, also comprises a triptan, especially sumatriptan, naratriptan, zolmitriptan, eletriptan, almotriptan, frovatriptan, and/or rizatriptan.

GABA modulators are particularly carbamazepine, oxcarbazepine, baclofen, clonazepam, lamotrigine, gabapentin or pregabalin. Advantageously, it is carbamazepine, gabapentin or pregabalin.

In particular, Nav 1.7 sodium channel inhibitors are described in Zakrzewska J M et al., *Lancet Neurol* (2017), 16: 291-300 *"Safety and efficacy of a Nav1.7 selective sodium channel blocker in patients with trigeminal neuralgia: a double-blind, placebo-controlled, randomised withdrawal phase 2a trial"* whose contents are incorporated here for reference.

Compositions of the invention to treat trigeminal nerve pains, in particular migraines, especially acute migraines, can also comprise at least one cannabinoid derivative, in particular $\Delta^9$ THC, or a protector of its metabolism (Piomelli et al. *review, TIPS* (2000), 21: 218-224). It has actually been observed that the coadministration (simultaneous or staggered in time) of small doses of cannabinoids (in particular, $\Delta^9$ THC) potentiates the analgesic effects of the salts according to the invention (salts of the compound of formula (I) or salts of formula (II)) without significantly inducing the detrimental effects of cannabinoids, which appear intravenously (IV) at 4-5 mg/kg (sedation). In the sense of the present invention, "very low cannabinoid content" means cannabinoid contents less than those inducing said adverse side effects. In the sense of the present invention, "cannabinoids" means $\Delta^9$ THC, synthetic CB1 receptor agonists or inhibitors of anandamide degradation. The cannabinoids introduced into the composition according to the invention are preferably $\Delta^9$ THC.

According to a particular embodiment, the composition of the invention to treat trigeminal nerve pains, in particular migraines, especially acute migraines, also comprises a second active ingredient chosen from among morphine, $\Delta^9$ THC, carbamazepine, oxcarbazepine, baclofen, clonazepam, lamotrigine, gabapentin or pregabalin, Nav1.7 sodium channel blockers, CGRP inhibitors, advantageously the second active ingredient is selected from morphine, $\Delta^9$ THC, gabapentin or Ia pregabalin.

Another object of the invention is a kit comprising:
1) a first composition comprising at least one compound of formula (I) such as defined previously, and
ii) a second composition comprising at least one second active ingredient useful to treat trigeminal nerve pain, in particular migraines, for example acute migraines, especially selected from analgesics, nonsteroidal antiinflammatory drugs (NSAIDs), opioids, triptans, GABA modulators and/or cannabinoids (advantageously chosen from morphine, $\Delta^9$ THC, oxcarbamazepine, baclofen, clonazepam, lamotrigine, gabapentin or pregabalin, Nav1.7 sodium channel blockers and CGRP inhibitors, preferably morphine, $\Delta^9$ THC, gabapentin or pregabalin), as combination products for simultaneous, separate, or staggered use.

This kit can be used as a drug, especially in the treatment of trigeminal nerve pains, such as migraine, trigeminal neuralgia or neuropathic pain associated with multiple sclerosis. Preferably, this kit is used to treat acute migraines.

The present invention also concerns a composition comprising a quantity comprised between 50 mg and 800 mg, of a salt of a compound of formula (I) or a salt of formula (II), in particular of compound 1.

According to a first variant, the present invention also concerns a composition comprising a quantity comprised between 200 mg and 800 mg, of a salt of a compound of formula (I) or a salt of formula (II), in particular of compound 1.

According to a second variant, the present invention also concerns a composition comprising a quantity comprised between 100 mg and 400 mg, of a salt of a compound of formula (I) or a salt of formula (II), in particular of compound 1.

According to a third variant, the present invention also concerns a composition comprising a quantity comprised between 50 mg and 200 mg, of a salt of a compound of formula (I) or a salt of formula (II), in particular of compound 1.

According to one embodiment, the compositions such as described above are used for the treatment of trigeminal nerve pains. Preferably, these compositions are used for the treatment of migraines, for example acute migraines.

Advantageously, these compositions may be administered to the patient suffering from trigeminal nerve pains, in particular migraines, by following the dosage regimen described above.

DESCRIPTION OF FIGURES

FIG. 1: Tail withdrawal latency time (in seconds), for the control group (with the carrier or 20 minutes after IP injection of a dose of 50 mg/kg of compound 1), and for the EAE model group (with the carrier or 20 minutes after injection of a dose of 50 mg/kg or 100 mg/kg of compound 1). Nociceptive thresholds are measured on D21, D28 and D35. Representation is done on D28. *: p<0.05 versus carrier control group or EAE (ANOVA+Newman-Keuls).

| Nociceptive threshold (in seconds, Dn = threshold measurement day, 20 min after administration of compound 1 (PL37)) | | | |
|---|---|---|---|
| Day | Before Injection | Compound 1, 50 mg/kg | Compound 1, 100 mg/kg | Control |
| D 21 | 2.69 | 5.12 (4) | | |
| D 28 | 3.0/2.69 | 4.14 (5) | 5.98 (5) | 4.85 (7) |
| D 35 | 2.69 | | 5.46 (5) | 4.85 (7) |

Figure 2:
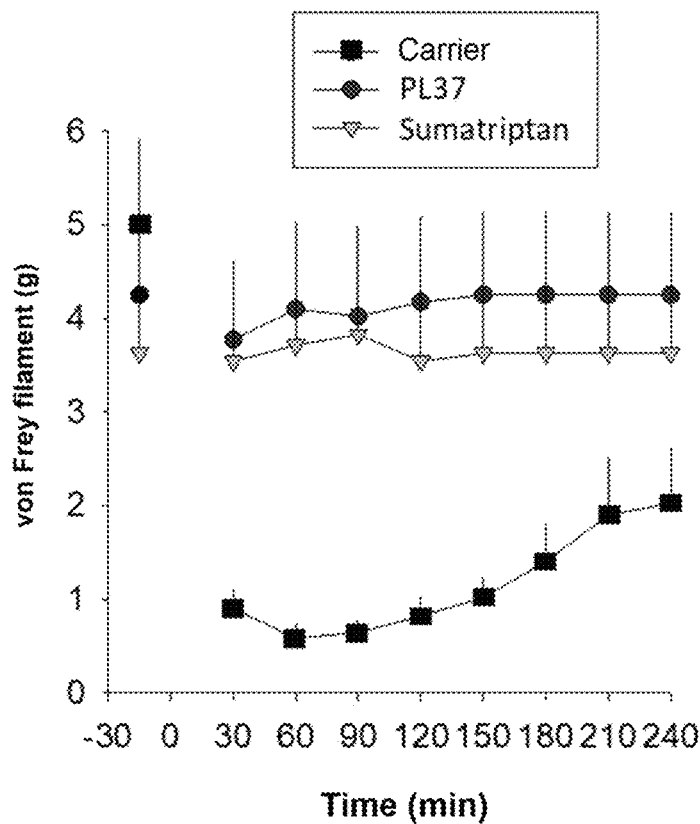
FIG. 2 is graph showing the von Frey force necessary to bring about head withdrawal (in g) as a function of time (minutes) after IV injection of a saline solution (carrier, black square), a solution of compound 1 (black circle), or sumatriptan (gray triangle).

FIG. 2: Headache/chronic migraine (chronic administration of ISDN): Von Frey force necessary to bring about head withdrawal (in g) as a function of time, measured in minutes, after IV injection of a saline solution (carrier, black square), a solution of compound 1 (black circle) or sumatriptan (gray triangle).

Figure 3:
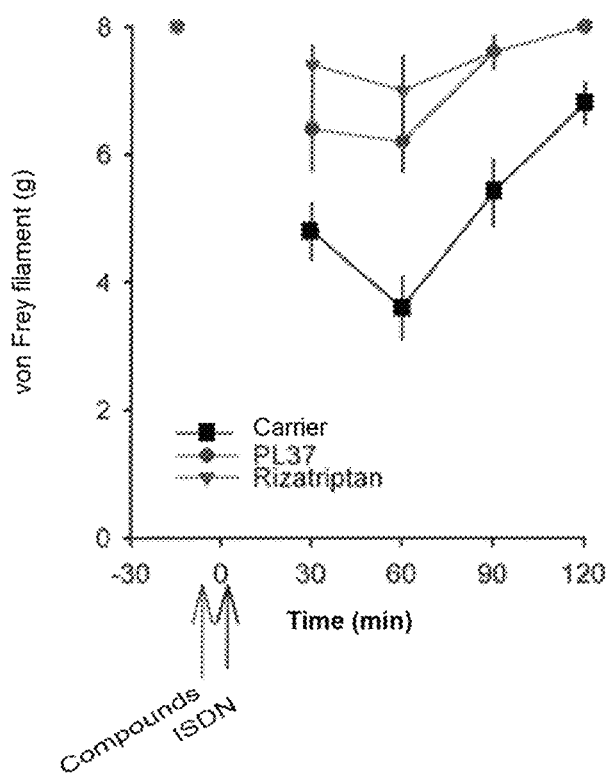
FIG. 3 is graph showing the von Frey force necessary to bring about head withdrawal (in g) as a function of time (minutes) after oral administration of a saline solution (carrier, black square), a solution of compound 1 (black circle) or rizatriptan (gray triangle)

FIG. 3: Acute headache (1 administration of ISDN): Von Frey force necessary to bring about head withdrawal (in g) as a function of time, measured in minutes, after oral administration of a saline solution (carrier, black square), a solution of compound 1 (black circle) or rizatriptan (gray triangle).

Figure 4:
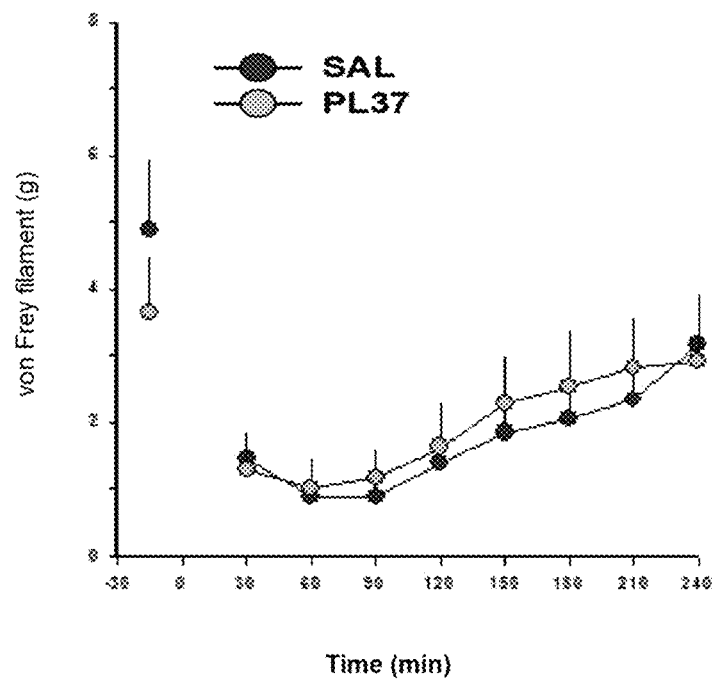
FIG. 4 is a graph showing the von Frey force necessary to bring about head withdrawal (in g) as a function of time (minutes) after oral administration of a saline solution (carrier, black circle) or compound 1 (PL37, gray circle, 50 mg/kg)

FIG. 4: Headache/chronic migraine (chronic administration of ISDN): Von Frey force necessary to bring about head withdrawal (in g) as a function of time, measured in minutes, after oral administration of a saline solution (carrier, black circle) or compound 1 (PL37) (gray circle, 50 mg/kg)

Figure 5:
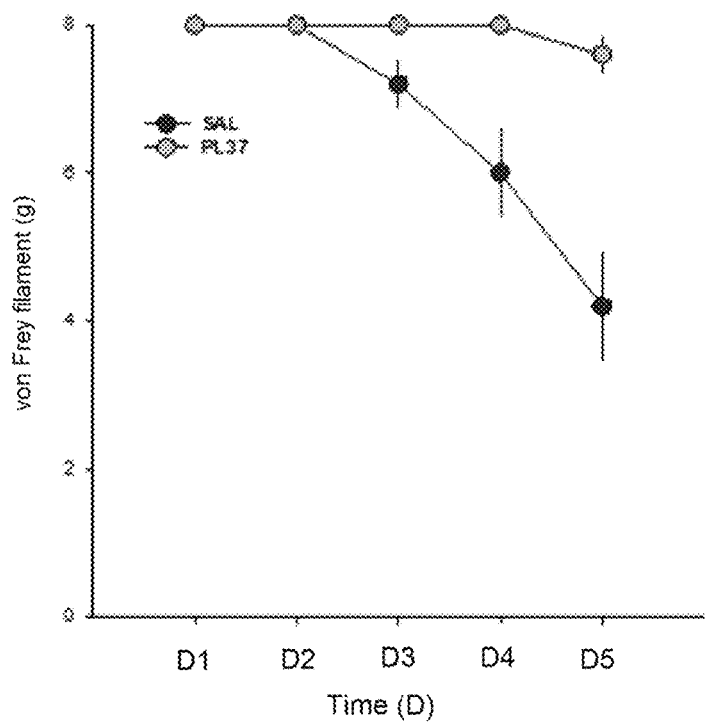
FIG. 5 is a graph showing the von Frey force necessary to bring about head withdrawal (in g) as measured at t=0 before oral administration of saline solution (carrier, black circle) or compound 1 (gray circle, 50 mg/kg) measured for 5 days.
Figure 6:
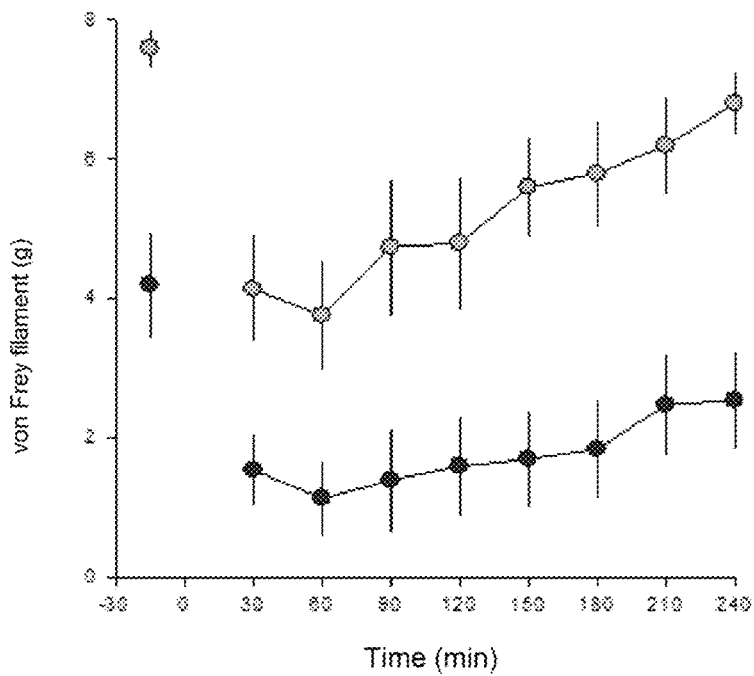
FIG. 6 is a graph showing the von Frey force necessary to bring about head withdrawal (in g) as a function of time (minutes) after oral administration of a saline solution (carrier, black circle) or compound 1 (gray circle, 50 mg/kg once daily).

FIG. 5: Headache/chronic migraine (chronic administration of ISDN and compound 1 (PL37))—Cutaneous sensitivity before administration of compound 1: Von Frey force necessary to bring about head withdrawal (in g) as a measured at t=0, before oral administration of a saline solution (carrier, black circle) or compound (gray circle, 50 mg/kg) measured for 5 days FIG. 6: Headache/chronic migraine (chronic administration of ISDN and compound 1 (PL37)): Von Frey force necessary to bring about head withdrawal (in g) as a function of time, measured in minutes, after oral administration of a saline solution (carrier, black circle) or compound 1 (gray circle, 50 mg/kg) once daily

EXAMPLES

The invention will be further illustrated, without being limited, by the examples below.

Example 1: Multiple Sclerosis Model (Experimental Autoimmune Encephalitis, EAE)

The multiple sclerosis model can be induced in SJL mice, female albino white mice, by the administration of an emulsion made up of a myeline fragment and complete Freund's adjuvant (Aicher et al., *Pain* (2004), 110: 560-570). Central nervous system inflammation appears at the end of around ten days=experimental autoimmune encephalomyelitis, or EAE.

Female SJL mice, purchased from Charles River Laboratories, arrive at the age of 5 weeks and are immunized at the age of 6 weeks. Each mouse receives, under mask anesthesia (2% isoflurane), an emulsion of a volume of 200 μL in the left flank, containing 150 μg of $PLP_{139-151}$ (Proteolipid Protein Myelin, fragment 139-151) in 100 μL of sterile 0.9% NaCl as well as 100 μL of incomplete Freund's adjuvant (Sigma) completed by inactivated *Mycobacterium tuberculosis* (Difco, USA) at 4 mg/mL=complete adjuvant.

The symptoms of the disease are reported between D10 and D15, which is reflected by an acute phase, during which scores are high and the animals present a loss of pain sensitivity. This phase precedes a chronic phase which starts around D18 and is characterized by stabilization of the animals general condition and the onset of a significant lowering in the pain perception threshold (hyperalgic state) (Aicher et al., *Pain* (2004), 110: 560-570).

Nociceptive thresholds were determined from D12 by the tail immersion test.

Compound 1 is administered IP (intraperitoneally) at 50 mg/kg and 100 mg/kg in a EtOH/Tween 80/Water carrier (10/10/80) (100 μL per 10 g of mice). The measurement of time of tail withdrawal from a 48° C. bath is done at 20 min after injection (cut-off=10 sec).

The administration of compound 1 (PL37) at 50 and 100 mg/kg IP permits reducing hyperalgesia in mice in a multiple sclerosis experimental autoimmune encephalomyelitis (EAE) model (see FIG. 1).

Example 2: Migraine Attack Model

Migraine is a neurovascular disorder characterized by recurrent headache attacks accompanied by variable neurological problems, including cephalic cutaneous allodynia. This symptom is most common in migraine patients. It affects 60 to 80% of chronic migraine patients (Guy et al., *Cephalalgia* (2010), 30: 881-886; Lovatti, *Expert Rev Neurother* (2009), 9: 395-408; Louter et al., *Brain* (2013), 136: 3489-3496). Moreover, the onset of allodynia is considered to be a risk factor for chronic migraine (Louter et al., *Brain* (2013), 136: 3489-3496) and is also indicative of a state of central sensitization (Boyer et al., *Pain* (2014), 155: 1196-1205).

a) Persistent Allodynia Model Induced by Recurrent Systemic Administration of Isosorbide Dinitrate (Migraine/Chronic Headache)

The effects of systemic administration of compound 1 on mechanical cephalic allodynia were tested in rats in a migraine model induced by repeated systemic injection of an NO donor, isosorbide dinitrate (ISDN). Indeed, the powerful vasodilating action of "NO donors" explains their particular propensity to trigger headache in healthy subjects and migraine attacks in migraine patients (Hansen & Olesen, *Cephalalgia* (2017), 37: 11-19).

Animals

The experiments were conducted on male Sprague-Dawley CD rats (200-250 g, Charles River Laboratories). A minimum delay of 7 days was respected before any experimentation.

Assessment of Cephalic Cutaneous Sensitivity

The animals were first subjected to habituation sessions designed to reproduce the animal's environmental conditions and handling by the experimenter during the final test.

The mechanical sensitivity of the periorbital region was measured by the von Frey test, which consists of applying a range of von Frey filaments in this region, calibrated to exert a constant force (expressed in grams) to determine the force (threshold) that leads to a head withdrawal reaction. The rats were habituated to these tests for 5 days preceding the experiment for one hour, so that repeated measurements give reproducible results. At the end of the habituation period, the mechanical pain sensitivity thresholds were 8 g on average (Boyer et al., *Pain* (2014), 155: 1196-1205; Dallel et al., *Cephalalgia* (2017), January 1:333102417714032. doi: 10.1177/0333102417714032). These values are not very painful since they consist of measuring a threshold with the possibility of escape and do not lead to reactions other than head withdrawal. The rats then received successive intraperitoneal injections of ISDN (10 mg/kg) and cutaneous sensitivity was assessed by means of the von Frey test. Mechanical allodynia developed progressively, reflected by a reduction in the values of the force necessary (thresholds) to induce head withdrawal. On the day of the experiment, the forces exerted by the von Frey filaments that led to head withdrawal were measured in each rat under controlled conditions every 30 minutes for 4 hours.

Assessment of Antimigraine Activity

On the day of experimentation, the rats received a first injection (intravenous) of physiological saline, sumatriptan or compound 1 followed, 5 minutes later, by a second intraperitoneal injection of ISDN (10 mg/kg). The rat was then replaced in the observation box. The forces inducing head withdrawal were measured every 30 minutes for 4 hours, to follow the kinetics of the effect.

3 groups were made up:
1 control group: intravenous injection of physiological saline (n=10)
1 test group: intravenous injection of compound 1 (20 mg/kg; n=10)
1 reference group: intravenous injection of sumatriptan (300 µg/kg; n=10)

Data Analysis

A two-way analysis of variance (effect of time and treatment) was done by repeated measurements and was followed by a post-hoc test. The results are presented in FIG. 2.

It is observed that compound 1—administered intravenously at the dose of 20 mg/kg—considerably reduces cephalic cutaneous sensitivity, which is significant for a reduction in associated migraine activity, in chronic conditions.

b) Mechanical Allodynia Model Induced by Single Administration of Isosorbide Dinitrate (Acute Migraine/Headache)

The effects of systemic administration of compound 1 on mechanical cephalic allodynia were tested in rats in a migraine model induced by single systemic injection of an NO donor, isosorbide dinitrate (ISDN). Indeed, the powerful vasodilating action of "NO donors" explains their particular propensity to trigger headache in healthy subjects and migraine attacks in migraine patients (Hansen & Olesen, *Cephalalgia* (2017), 37: 11-19).

Animals

The experiments were conducted on male Sprague-Dawley CD rats (200-250 g, Charles River Laboratories). A minimum delay of 7 days was respected before any experimentation.

Assessment of Cephalic Cutaneous Sensitivity

The animals were first subjected to habituation sessions designed to reproduce the animals environmental conditions and handling by the experimenter during the final test.

The mechanical sensitivity of the periorbital region was measured by the von Frey test, which consists of applying a range of von Frey filaments in this region, calibrated to exert a constant force (expressed in grams) to determine the force (threshold) that leads to a head withdrawal reaction. The rats were habituated to these tests for 5 days preceding the experiment for one hour, so that repeated measurements give reproducible results. At the end of the habituation period, the mechanical pain sensitivity thresholds were 8 g on average (Boyer et al., *Pain* (2014), 155: 1196-1205; Dallel et al., *Cephalalgia* (2017), January 1:333102417714032. doi: 10.1177/0333102417714032). These values are not very painful since they consist of measuring a threshold with the possibility of escape and do not lead to reactions other than head withdrawal. The rats then received an intraperitoneal injection of ISDN (10 mg/kg) and cutaneous sensitivity was assessed by means of the von Frey test. Mechanical allodynia developed progressively, reflected by a reduction in the values of the force necessary (thresholds) to induce head withdrawal. On the day of the experiment, the forces exerted by the von Frey filaments that led to head withdrawal were measured in each rat under controlled conditions every 30 minutes for 4 hours.

Assessment of Antimigraine Activity

On the day of experimentation, the rats received a first injection (oral) of physiological saline, rizatriptan (10 µg/kg) or compound 1 (50 mg/kg) followed, 5 minutes later, by an intraperitoneal injection of ISDN (10 mg/kg). The rat was then replaced in the observation box. The forces inducing head withdrawal were measured every 30 minutes for 4 hours, to follow the kinetics of the effect.

3 groups were made up:
1 control group: oral administration of physiological saline (n=10)
1 test group: oral administration of compound 1 (50 mg/kg; n=10)
1 reference group: oral administration of rizatriptan (10 µg/kg; n=10)

Data Analysis

A two-way analysis of variance (effect of time and treatment) was done by repeated measurements and was followed by a post-hoc test. The results are presented in FIG. 3.

It is observed that compound 1—administered orally at the dose of 50 mg/kg—considerably reduces cephalic cutaneous sensitivity, which is significant for a reduction in the intensity of the acute migraine attack.

Example 3: Model for Prevention of Migraine Attacks by Oral Administration

The effects of oral administration of compound 1 on mechanical cephalic allodynia were tested in rats in a chronic migraine model induced by repeated systemic injection of an NO donor, isosorbide dinitrate (ISDN). Indeed, the powerful vasodilating action of "NO donors" explains their particular propensity to trigger headache in healthy subjects and migraine attacks in migraine patients (Hansen & Olesen, *Cephalalgia* (2017), 37: 11-19).

Animals

The experiments were conducted on male rats (10 rats per group of the Sprague-Dawley CD strain (200-250 g, Charles River Laboratories), randomly assigned into each group before experimentation. A minimum delay of 7 days was respected before any experimentation. The experiments were conducted with the experimenter blinded.

Assessment of Cephalic Cutaneous Sensitivity

The animals were first subjected to habituation sessions designed to reproduce the animals environmental conditions and handling by the experimenter during the final test.

The mechanical sensitivity of the periorbital region was measured by the von Frey test, which consists of applying a range of von Frey filaments in this region, calibrated to exert a constant force (expressed in grams) to determine the force (threshold) that leads to a head withdrawal reaction. The rats were habituated to these tests for 5 days preceding the experiment for one hour, so that repeated measurements give reproducible results. At the end of the habituation period, the mechanical pain sensitivity thresholds were 8 g on average (Boyer et al., *Pain* (2014), 155: 1196-1205; Dallel et al., *Cephalalgia* (2017), January 1:333102417714032. doi: 10.1177/0333102417714032). These values are not very painful since they consist of measuring a threshold with the possibility of escape and do not lead to reactions other than head withdrawal. The rats then received successive intraperitoneal injections of ISDN (10 mg/kg) and cutaneous sensitivity was assessed by means of the von Frey test.

Example 4: Dosage Regimen for Compound 1—Study of Adverse Effects Observed During Phase 1b of the Clinical Study for Compound 1 (PL37)

Details on the Experimental Conditions

Forty healthy volunteers aged 18 to 65 randomly divided into five groups of 8 subjects (6 groups receiving four daily doses of compound 1 (PL37), and two groups receiving four daily doses of placebo)

The doses indicated in the following table were administered 4 times a day for 5 days, the daily dose varying from 800 to 4000 mg, the total quantity over five days being comprised between 4000 and 20,000 mg.

| Subjects with: | Compound 1 (PL37) | | | | | Placebo N = 10 n (%) E | Total N = 40 n (%) E |
| | 200 mg N = 6 n (%) E | 400 mg N = 6 n (%) E | 600 mg N = 6 n (%) E | 800 mg N = 6 n (%) E | 1000 mg N = 6 n (%) E | | |
|---|---|---|---|---|---|---|---|
| TEAEs | 1(16.7)3 | 5(83.3)12 | 4(66.7)7 | 6(100.0)10 | 4(66.7)15 | 5(50.0)10 | 25(62.5)57 |
| LAE | 0 | 0 | 0 | 0 | 0 | 0 | 0 |
| SAE | 0 | 0 | 0 | 0 | 0 | 0 | 0 |
| Death | 0 | 0 | 0 | 0 | 0 | 0 | 0 |

E = number of adverse reactions
n = number of subjects who had adverse reactions
N = number of subjects per treatment group
LAE = limiting adverse event
TEAEs = treatment-emergent adverse event
SAE = serious adverse event Mechanical allodynia developed progressively, reflected by a reduction in the values of the force necessary (thresholds) to induce head withdrawal.

Cutaneous mechanical sensitivity was measured before and on the test day (FIG. 4, single administration of compound 1 or FIG. 6, repeated administration of compound 1) or before and on the test day (Days 1, 2, 3, 4 and 5) (FIG. 5, repeated administration of compound 1) before injection and at 30 min intervals for 4 h in the different groups of rats receiving intraperitoneal ISDN (10 mg/kg, volume of 10 mL/kg).

Assessment of Antimigraine Activity

On the day of experimentation, the rats received a first oral administration of carrier (10% EtOH in 0.9% NaCl physiological saline) or compound 1 (50 mg/kg in the carrier) followed, 5 minutes later, by a second intraperitoneal injection of ISDN (10 mg/kg). The rat was then replaced in the observation box. The forces inducing head withdrawal were measured every 30 minutes for 4 hours, to follow the kinetics of the effect.

Data Analysis

A two-way analysis of variance (effect of time and treatment) was done by repeated measurements and was followed by a post-hoc test.

Compound 1—administered orally at the dose of 50 mg/kg once on the experiment day (FIG. 4) had no effect on cutaneous cephalic sensitivity. Compound 1, administered repeatedly over several days (5 days) significantly reduces cutaneous cephalic sensitivity compared to the carrier one day compared to the previous one, before administration of ISDN (FIG. 5) or as a function of time, after administration of ISDN (FIG. 6), which is significant for prevention and reduction of associated migraine activity, in chronic condition.

The invention claimed is:

1. A method for preventing or treating a trigeminal-nerve related pain in a subject in need thereof, comprising administering to the subject a pharmaceutically-acceptable salt of a compound of formula (I):

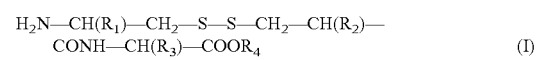

$$\text{H}_2\text{N—CH(R}_1\text{)—CH}_2\text{—S—S—CH}_2\text{—CH(R}_2\text{)—CONH—CH(R}_3\text{)—COOR}_4 \quad \text{(I)}$$

wherein:

$R_1$ is:
(i) a saturated or unsaturated, linear or branched hydrocarbon chain, containing 1 to 6 carbon atoms, optionally substituted by:
  an OR, SR or S(O)R radical, wherein R is a hydrogen, a linear or branched hydrocarbon chain of 1 to 4 carbon atoms, a phenyl radical or a benzyl radical, or
  a phenyl or benzyl radical,
(ii) a phenyl or benzyl radical optionally substituted by:
  1 to 5 halogens, or,
  an OR, SR or S(O)R radical, wherein R is a hydrogen, a linear or branched hydrocarbon chain of 1 to 4 carbon atoms, a phenyl radical, or a benzyl radical, or
  a methylene radical substituted by a 5 or 6 atom heterocycle, aromatic or saturated, having a nitrogen or sulfur atom as heteroatom, optionally oxidized in the form of N-oxide or S-oxide;

$R_2$ is:
(i) a phenyl or benzyl radical optionally substituted by:
  1 to 5 halogens,
  an OR or SR radical, wherein R is a hydrogen, a linear or branched hydrocarbon chain of 1 to 4 carbon atoms, a phenyl radical, or a benzyl radical, an amino group, optionally mono— or disubstituted by a cyclic or linear aliphatic group, of 1 to 6 carbon atoms,
a 5 or 6 atom aromatic ring, or
an aromatic heterocycle ring with 5 to 6 atoms, the heteroatom being an oxygen, nitrogen or sulfur, or
(ii) a methylene group substituted by a 5 or 6 atom heterocycle, aromatic or saturated, being an oxygen, nitrogen or sulfur, the nitrogen and sulfur atoms optionally being oxidized in the form of N-oxide or S-oxide;
$R_3$ is:
(i) a hydrogen,
(ii) an OH or OR group, wherein R is a hydrogen, a linear or branched hydrocarbon chain of 1 to 4 carbon atoms, a phenyl radical, or a benzyl radical,
(iii) a saturated hydrocarbon (alkyl) chain, linear or branched, having 1 to 6 carbon atoms, optionally substituted by an OR or SR radical, R is a hydrogen, a linear or branched hydrocarbon chain of 1 to 4 carbon atoms, a phenyl radical, or a benzyl radical,
(iv) a phenyl radical or a benzyl radical, optionally substituted by 1 to 5 halogens, or
(v) an OR or SR group, wherein R is a hydrogen, a linear or branched hydrocarbon chain of 1 to 4 carbon atoms, a phenyl radical, or a benzyl radical, and
$OR_4$ is:
(i) a glycolate $OCH_2COOR'$ or lactate $OCH(CH_3)COOR'$ radical,
(ii) an $OCH(R'')O(CO)OR'$ or $OCH(R'')O(CO)R'$ group,
(iii) an $OCH(CH_2OCOR')_2$ or $OCH_2$—$CH(OCOR')$—$CH_2OCOR'$ triglyceride radical,
(iv) a glycoside radical,
(v) a sulfonate $OCH_2CH_2(SO_2)CH_3$ radical, or
(vi) an $OCH(CH_2OH)_2$ radical,
R' is:
a linear or branched $C_1$-$C_6$ alkyl optionally substituted by a $C_1$—$C_3$ alkoxy group,
a $C_5$-$C_8$, cycloalkyl group,
a phenyl group,
a benzyl group,
a heteroaryl group, or
an alkyl heteroaryl group; and
—R" is:
a hydrogen atom,
a linear or branched $C_1$-$C_6$ alkyl chain optionally substituted by a $C_1$-$C_3$ alkoxy group,
a $C_5$-$C_8$, cycloalkyl group,
a phenyl group,
a benzyl group,
a heteroaryl group, or
an alkyl heteroaryl group.

2. The method according to claim 1, wherein $R_1$ is an alkyl radical having 1 to 4 carbon atoms substituted by an SR radical.

3. The method according to claim 1, wherein radical $R_2$ is a benzyl radical or a methylene radical substituted by a 5 or 6 atom heterocycle, aromatic or saturated, having nitrogen or sulfur as heteroatom, optionally oxidized in the form of N-oxide or S-oxide.

4. The method of claim 1, wherein $R_3$ is a hydrogen atom or an alkyl radical with 1 to 6 carbon atoms substituted by an OH or SH radical.

5. The method of claim 1, wherein $OR_4$ is an $OCH(R'')O(CO)OR'$ or $OCH(R'')O(CO)R'$ group, radical R' being a $C_1$-$C_4$ alkyl chain, and radical R" being a methyl, $CH(CH_3)_2$, cyclohexyl or phenyl radical.

6. The method of claim 1, wherein the compound of formula (I) is in the form of a fumarate salt.

7. The method of claim 1, wherein the salt of a compound of formula (I) is a salt of formula (II):

$$A^-, H_3N^+\text{—}CH(R_1)\text{—}CH_2\text{—}S\text{—}S\text{—}CH_2\text{—}CH(R_2)\text{—}CONH\text{—}CH(R_3)\text{—}COOR_4 \quad (II)$$

wherein:
$A^-$ is a phosphate, chloride, acetate, methanesulfonate, borate, lactate, fumarate, succinate, hemisuccinate, citrate, tartrate, hemitartrate, maleate, ascorbate, hemifumarate, hexanoate, heptanoate, hippurate, hydrocinnamate, phenylglyoxylate or nicotinate anion;
$R_1$ is a saturated or unsaturated hydrocarbon chain, linear or branched, containing 1 to 6 carbon atoms, optionally substituted with an OR, SR or S(O)R group in which R represents a hydrogen, a linear or branched hydrocarbon chain of 1-4 carbons, a phenyl radical or benzyl radical;
(i) a phenyl or benzyl group optionally substituted by:
1 to 5 halogen atoms, a thiol, an ether OR, or a thioether SR, wherein R is a hydrogen, a linear or branched hydrocarbon chain of 1 to 4 carbon atoms, a phenyl radical, or a benzyl radical,
an aromatic ring or aromatic heterocycle with 5 to 6 atoms, the heteroatom being an oxygen, nitrogen or sulfur, or
(ii) a methylene group substituted by a 5 or 6 atom heterocycle, aromatic or saturated, the heteroatom being an oxygen, nitrogen or sulfur, the nitrogen or sulfur atoms optionally being oxidized in the form of N-oxide or S-oxide;
$R_3$ is:
(i) a hydrogen,
(ii) an OH or OR group, wherein R is a hydrogen, linear or branched hydrocarbon chain of 1 to 4 carbon atoms, a phenyl radical, or a benzyl radical,
(iii) a linear or branched $C_1$-$C_6$ alkyl, optionally substituted by an OH, OR, SH or SR group, R is a hydrogen, a linear or branched hydrocarbon chain 1 to 4 carbon atoms, a phenyl radical, or a benzyl radical, or
(iv) a phenyl or benzyl group, optionally substituted by 1 to 5 halogens, notably fluorine or by an OR or SR group, R is a hydrogen, a linear or branched hydrocarbon chain of 1 to 4 carbon atoms, a phenyl radical or a benzyl radical;
$OR_4$ is:
(i) a glycolate $OCH_2COOR'$ or lactate $OCH(CH_3)COOR'$ radical;
(ii) an $OCH_2OCOR'$ or $OCH(CH_3)OCOOR'$ group, or
(iii) an $OCH(CH_2OCOR')_2$ or $OCH_2$—$CH(OCOR')$—$CH_2OCOR'$ triglyceride radical,
wherin
R' is a linear or branched $C_1$-$C_4$ alkyl.

8. The method of claim 1, wherein the salt is a pharmaceutically-acceptable salt selected from the group consisting of:
1-(2-(1-(2,3-diacetoxypropoxycarbonyl)-ethylcarbamoyl)-3-thiophen-3-ylpropyl disulfanylmethyl)-3-methylsulfanylpropyl-amine,
1-(2-(1-(2-methanesulfonylethoxycarbonyl)-ethylcarbamoyl)-3-thiophen-3-ylpropyl disulfanylmethyl)-3-methylsulfanylpropyl-amine, 1-(2-(1-(1-ethoxycarbonyloxyethoxycarbonyl))-ethylcarbamoyl)-3-thiophen-3-yl-propyl disulfanylmethyl)-3-methylsulfanylpropyl-amine, 1-(2-(1-ethoxycarbonylmethyloxycarbonylethylcarbamoyl)-3-thiophen-3-yl-propyl disulfanylmethyl)-3-methylsulfanylpropyl-amine, 1-(2-(1-(1-ethoxycarbonyloxyethoxycarbonyl)-2-hydroxypropylcarbamoyl)-3-thiophen-3-ylpropyldisulfanylméthyl)-3-methylsulfanylpropyl-amine, 1-(2-(1-(2-acetoxy-1-acetoxymethylethoxycarbonyl)-ethylcarbamoyl)-3-thiophen-3-ylpropyldisulfanylmethyl)-3-methylsulfanylpropyl-amine, 1-(2-(1-(2-hydroxy-1-hydroxymethylethoxycarbonyl)-ethylcarbamoyl)-3-thiophen-3-ylpropyldisulfanylmethyl)-3-methylsulfanylpropyl-amine, 1-(2-(1-(3,4,5,6-tetrahydroxytetrahydropyran-2-yl-methoxycarbonyl)-ethylcarbamoyl)-3-thiophen-3-yl-propyldisulfanylmethyl)-3-methylsulfanylpropyl-amine, 1-(2-(1-(1-ethoxycarbonyloxy-ethoxycarbonyl)-2-hydroxypropylcarbamoyl)-3-phenyl propyldisulfanylmethyl)-3-methylsulfanylpropyl-amine, 1-(2-(1-(2-acetoxy-1-acetoxymethyl-ethoxycarbonyl)-2-hydroxypropylcarbamoyl)-3-phenylpropyldisulfanylmethyl)-3-methylsulfanylpropyl-amine, 1-(2-((1-ethoxycarbonyloxy-ethoxycarbonylmethyl)-carbamoyl)-3-phenyl-propyl disulfanylmethyl)-3-methylsulfanylpropyl-amine, 3-(2-amino-4-methylsulfanyl-butyldisulfanyl)-2-benzyl-N-(5-ethyl-(1,3,4)-thiadiazol-2-yl)-propionamide, 1-(2-((1-ethoxycarbonyloxy-2-methyl-propoxycarbonylméthyl)-carbamoyl)-3-phenyl-propyldisulfanylmethyl)-3-methylsulfanyl-propyl-amine, 1-(2-((cyclohexyl-ethoxycarbonyloxy-methoxycarbonylmethyl)-carbamoyl)-3-phenyl-propyldisulfanylmethyl)-3-methylsulfanyl-propyl-amine, 1-(2-((ethoxycarbonyloxy-phenyl-methoxycarbonylmethyl)-carbamoyl)-3-phenyl-propyldisulfanylmethyl)-3-methylsulfanyl-propyl-amine, 3-methylsulfanyl-1-(3-phenyl-2-((1-propionyloxy-ethoxycarbonylmethyl)-carbamoyl)-propyldisulfanylmethyl)-propyl-amine, 1-(2-((2-methyl-1-propionyloxy-propoxycarbonylmethyl)-carbamoyl)-3-phenyl-propyldisulfanylmethyl)-3-methylsulfanyl-propyl-amine, 1-(2-((cyclohexyl-propionyloxy-methoxycarbonylmethyl)-carbamoyl)-3-phenyl-propyldisulfanylmethyl)-3-methylsulfanyl-propyl-amine, 3-methylsulfanyl-1-(3-phenyl-2-((phenyl-propionyloxy-methoxycarbonylmethyl)-carbamoyl)-propyldisulfanylmethyl)-propyl-amine.

9. The method of claim 1, wherein the salt is (5S,10S)-10-benzyl-16-methyl-11,14,18-trioxo-15,17,19-trioxa-2,7,8-trithia-12-azahenicosan-5-aminium fumarate.

10. The method of claim 1, comprising administering a therapeutic dose of the salt to the patient in need thereof in one to four administrations.

11. The method of claim 1, comprising administering a therapeutic dose comprising between 200 and 800 mg of the salt to the patient in need thereof.

12. The method of claim 1, comprising administering the salt for preventing migraine attacks.

13. The method of claim 1, comprising administering the salt for preventing or treating migraines or trigeminal neuralgia.

14. The method of claim 1, comprising administering the salt for preventing or treating essential trigeminal neuralgia, symptomatic trigeminal neuralgia, migraines, cephalic cutaneous allodynia, cluster headaches, or peripheral trigeminal pain associated with multiple sclerosis.

* * * * *